(12) United States Patent
Hon

(10) Patent No.: US 10,045,564 B2
(45) Date of Patent: Aug. 14, 2018

(54) ELECTRONIC CIGARETTE

(71) Applicant: FONTEM HOLDINGS 1 B.V., Amsterdam (NL)

(72) Inventor: Lik Hon, North Point (HK)

(73) Assignee: FONTEM HOLDINGS 1 B.V., Amsterdam (NL)

(*) Notice: Subject to any disclaimer, the term of this patent is extended or adjusted under 35 U.S.C. 154(b) by 0 days.

(21) Appl. No.: 15/633,434

(22) Filed: Jun. 26, 2017

(65) Prior Publication Data

US 2017/0325509 A1 Nov. 16, 2017

Related U.S. Application Data

(60) Continuation of application No. 14/525,066, filed on Oct. 27, 2014, which is a continuation of application No. 13/777,927, filed on Feb. 26, 2013, now Pat. No. 8,893,726, which is a division of application No. 13/560,789, filed on Jul. 27, 2012, now Pat. No. (Continued)

(30) Foreign Application Priority Data

Apr. 14, 2004 (CN) .................... 2004 2 0031182 U

(51) Int. Cl.
| | |
|---|---|
| A24F 47/00 | (2006.01) |
| H05B 1/02 | (2006.01) |
| H05B 3/00 | (2006.01) |
| A61M 11/00 | (2006.01) |
| A61M 11/04 | (2006.01) |
| A61M 15/00 | (2006.01) |

(Continued)

(52) U.S. Cl.
CPC ......... *A24F 47/008* (2013.01); *A61M 11/005* (2013.01); *A61M 11/044* (2014.02); *A61M 15/0085* (2013.01); *A61M 15/06* (2013.01); *A61M 16/0003* (2014.02); *H05B 1/0291* (2013.01); *H05B 3/0004* (2013.01); *A61M 2016/0024* (2013.01); *A61M 2016/0027* (2013.01); *A61M 2205/587* (2013.01); *A61M 2205/8206* (2013.01)

(58) Field of Classification Search
CPC .............................. A24F 47/00; A24F 47/008
See application file for complete search history.

(56) References Cited

U.S. PATENT DOCUMENTS

| | | |
|---|---|---|
| 705,919 A | 7/1902 | Gill |
| 1,147,416 A | 7/1915 | MacDonald |

(Continued)

FOREIGN PATENT DOCUMENTS

| | | |
|---|---|---|
| AU | 2004234199 | 11/2004 |
| BR | 9406968 | 8/1996 |

(Continued)

OTHER PUBLICATIONS

Andrus, Paul G. et al., Nicotine Microaerosol Inhaler, Canadian Respiratory Journal (1999) 6(6) p. 509-512.

(Continued)

*Primary Examiner* — Seyed Masoud Malekzadeh
*Assistant Examiner* — Dionne W Mayes
(74) *Attorney, Agent, or Firm* — Perkins Coie LLP; Kenneth H. Ohriner

(57) ABSTRACT

An electronic cigarette includes a shell and a mouthpiece. The external wall of the shell has an air inlet. An atomizer and a liquid-supply are in contact with each other. The air inlet, atomizer, and an aerosol passage are interconnected.

19 Claims, 5 Drawing Sheets

Related U.S. Application Data 8,490,628, which is a continuation of application No. 12/944,123, filed on Nov. 11, 2010, now Pat. No. 8,393,331, which is a continuation of application No. 10/587,707, filed as application No. PCT/CN2005/000337 on Mar. 18, 2005, now Pat. No. 7,832,410.

(51) Int. Cl.
*A61M 15/06* (2006.01)
*A61M 16/00* (2006.01)

(56) References Cited

U.S. PATENT DOCUMENTS

| | | |
|---|---|---|
| 1,514,682 A | 11/1924 | Wilson |
| 1,775,947 A | 5/1927 | Robinson |
| 2,057,353 A | 10/1936 | Whittemore |
| 2,631,219 A | 1/1953 | Suchy |
| 3,060,429 A | 10/1962 | Winston |
| 3,200,819 A | 8/1965 | Gilbert |
| 3,203,025 A | 8/1965 | Shreur |
| 3,313,393 A | 4/1967 | Katsuda |
| 3,385,303 A | 5/1968 | Hind |
| 3,400,998 A | 9/1968 | Daugherty |
| 3,428,053 A | 2/1969 | Schoenbaum |
| 3,431,393 A | 3/1969 | Katsuda |
| 3,471,120 A | 10/1969 | Geiselman et al. |
| 3,479,561 A | 11/1969 | Janning |
| 3,502,588 A | 3/1970 | Winberg |
| 3,685,522 A | 8/1972 | Kleinhans |
| 3,747,120 A | 7/1973 | Stemme |
| 3,795,561 A | 3/1974 | Bond et al. |
| 3,860,012 A | 1/1975 | Selke |
| 3,952,798 A | 4/1976 | Jacobson |
| 4,030,083 A | 6/1977 | Boll |
| 4,171,000 A | 10/1979 | Uhle |
| 4,270,552 A | 6/1981 | Jenkins |
| 4,589,428 A | 5/1986 | Keritsis |
| 4,641,053 A | 2/1987 | Takeda |
| 4,676,237 A | 6/1987 | Wood |
| 4,712,295 A | 12/1987 | Peele et al. |
| 4,735,217 A | 4/1988 | Gerth |
| 4,756,318 A | 7/1988 | Clearman |
| 4,771,295 A | 9/1988 | Baker |
| 4,771,796 A | 9/1988 | Myer |
| 4,797,692 A | 1/1989 | Ims |
| 4,848,374 A | 7/1989 | Chard |
| 4,878,506 A | 11/1989 | Pinck |
| 4,909,939 A | 3/1990 | Rickelton et al. |
| 4,945,448 A | 7/1990 | Bremenour |
| 4,945,929 A | 8/1990 | Egilmex |
| 4,945,931 A | 8/1990 | Gori |
| 4,947,874 A | 8/1990 | Brooks |
| 4,947,875 A | 8/1990 | Brooks |
| 4,968,263 A | 11/1990 | Silbernagel |
| 4,972,855 A | 11/1990 | Kuriyama |
| 4,976,692 A | 12/1990 | Atad |
| 4,981,522 A | 1/1991 | Nichols |
| 4,990,939 A | 2/1991 | Sekiya |
| 5,036,633 A | 8/1991 | Kobori et al. |
| 5,042,470 A | 8/1991 | Kanesaka |
| 5,060,671 A | 10/1991 | Counts |
| 5,095,921 A | 3/1992 | Losee |
| 5,124,200 A | 6/1992 | Mallonee |
| 5,129,409 A | 7/1992 | White |
| 5,144,962 A | 9/1992 | Counts |
| 5,159,940 A | 11/1992 | Hayward et al. |
| 5,162,263 A | 11/1992 | Counts |
| 5,179,966 A | 1/1993 | Losee |
| 5,224,265 A | 7/1993 | Dux |
| 5,249,586 A | 10/1993 | Morgan |
| 5,261,424 A | 11/1993 | Sprinkel |
| 5,266,746 A | 11/1993 | Nishihara |
| 1,016,844 A | 2/1994 | Moonelis |
| 5,322,075 A | 6/1994 | Deevi |
| 5,327,915 A | 7/1994 | Porenski |
| 5,432,251 A | 7/1995 | Grosse-Bley et al. |
| 5,438,978 A | 8/1995 | Hardester, III |
| 5,497,791 A | 3/1996 | Bowen |
| 5,505,214 A | 4/1996 | Collins |
| 5,591,368 A | 1/1997 | Fleischhauer |
| 5,646,666 A | 7/1997 | Cowger |
| 5,665,977 A | 9/1997 | Higgins |
| 5,666,978 A | 9/1997 | Counts |
| 5,703,633 A | 12/1997 | Gehrer |
| 5,730,158 A | 3/1998 | Collins |
| 5,743,251 A | 4/1998 | Howell |
| 5,745,985 A | 5/1998 | Ghosh |
| 5,799,663 A | 9/1998 | Gross |
| 5,819,756 A | 10/1998 | Mielordt |
| 5,894,841 A | 4/1999 | Voges |
| 5,944,025 A | 8/1999 | Cook |
| 5,996,589 A | 12/1999 | St. Charles |
| 6,010,052 A | 1/2000 | Leins et al. |
| 6,019,921 A | 2/2000 | Lutz |
| 6,040,560 A | 3/2000 | Fleischhauer |
| 6,062,213 A | 5/2000 | Fuisz |
| 6,102,036 A | 8/2000 | Slutsky |
| 6,155,268 A | 12/2000 | Takeuchi |
| 6,196,218 B1 | 3/2001 | Voges |
| 6,234,167 B1 | 5/2001 | Cox |
| 6,322,268 B1 | 11/2001 | Kaufmann |
| 6,354,293 B1 | 3/2002 | Madison |
| 6,357,671 B1 | 3/2002 | Cewers |
| 6,443,146 B1 | 9/2002 | Voges |
| 6,471,782 B1 | 10/2002 | Fang |
| 6,501,052 B2 | 12/2002 | Cox |
| 6,598,607 B2 | 7/2003 | Adiga |
| 6,601,776 B1 | 8/2003 | Oljaca |
| 6,620,659 B2 | 9/2003 | Emmma |
| 6,701,921 B2 | 3/2004 | Sprinkel |
| 6,722,763 B1 | 4/2004 | Hsu |
| 6,810,883 B2 | 11/2004 | Felter |
| 6,854,461 B2 | 2/2005 | Nichols |
| 6,854,470 B1 | 2/2005 | Pu |
| 6,986,607 B2 | 1/2006 | Roth et al. |
| 7,059,307 B2 | 6/2006 | Pellizzari |
| 7,100,618 B2 | 9/2006 | Dominguez |
| 7,143,766 B2 | 12/2006 | Schuster |
| 7,284,424 B2 | 10/2007 | Kanke |
| 7,315,599 B1 | 1/2008 | Morriss |
| 7,726,320 B2 | 6/2010 | Robinson |
| 7,830,031 B2 | 11/2010 | Helle et al. |
| 7,832,410 B2 | 11/2010 | Hon |
| 7,997,280 B2 | 8/2011 | Rosenthal |
| 8,156,944 B2 | 4/2012 | Han |
| 8,511,318 B2 | 8/2013 | Hon |
| 2001/0026788 A1 | 10/2001 | Piskorz |
| 2003/0011579 A1 | 1/2003 | Gong |
| 2003/0108342 A1 | 6/2003 | Sherwood |
| 2003/0109342 A1 | 6/2003 | Sherwood |
| 2003/0150446 A1 | 8/2003 | Patel |
| 2004/0149282 A1 | 8/2004 | Hickle |
| 2005/0016550 A1 | 1/2005 | Katase |
| 2006/0016453 A1 | 1/2006 | Kim |
| 2006/0093977 A1 | 5/2006 | Pellizzari |
| 2006/0196518 A1 | 9/2006 | Hon |
| 2007/0125765 A1 | 6/2007 | Nelson |

FOREIGN PATENT DOCUMENTS

| | | |
|---|---|---|
| CN | 1135860 A | 11/1996 |
| CN | 2293957 U | 10/1998 |
| CN | 1233436 | 11/1999 |
| CN | 1252961 A | 5/2000 |
| CN | 1530041 A | 9/2004 |
| CN | 1575673 A | 2/2005 |
| CN | 2719043 | 8/2005 |
| CN | 1541577 A | 9/2006 |
| CN | 201067079 Y | 6/2008 |
| CN | 201085044 Y | 7/2008 |
| CN | 201797997 U | 4/2011 |
| CN | 202026802 U | 11/2011 |
| CN | 202026804 U | 11/2011 |
| EP | 0295122 | 12/1988 |

(56) References Cited

FOREIGN PATENT DOCUMENTS

| | | |
|---|---|---|
| EP | 0342538 A | 11/1989 |
| EP | 0358002 | 3/1990 |
| EP | 0358114 A2 | 3/1990 |
| EP | 0230420 B1 | 3/1991 |
| EP | 0488488 B1 | 3/1992 |
| EP | 0545186 A2 | 6/1993 |
| EP | 0619761 A1 | 10/1994 |
| EP | 0430566 B1 | 4/1995 |
| EP | 0703735 | 4/1996 |
| EP | 0845220 A1 | 6/1998 |
| EP | 0951219 A1 | 11/2002 |
| EP | 0845220 B1 | 9/2003 |
| EP | 1736065 A1 | 12/2006 |
| JP | H9-326299 | 12/1997 |
| JP | 2001-291598 | 10/2001 |
| WO | WO1986002528 A2 | 5/1986 |
| WO | WO1994009842 | 5/1994 |
| WO | WO1994021317 | 9/1994 |
| WO | WO1997040876 | 11/1997 |
| WO | WO1998017130 | 4/1998 |
| WO | WO1998017131 A1 | 4/1998 |
| WO | WO2001005459 | 1/2001 |
| WO | WO2001032247 A1 | 5/2001 |
| WO | WO2002098390 A2 | 12/2002 |
| WO | WO2003000324 A1 | 3/2003 |
| WO | WO2003055486 | 7/2003 |
| WO | WO2003101454 | 12/2003 |
| WO | WO2004023222 | 3/2004 |
| WO | WO2004080216 | 3/2004 |
| WO | WO2004043175 A1 | 5/2004 |
| WO | WO2004095955 | 11/2004 |

OTHER PUBLICATIONS

Brazilian Industrial Property Institute, Office Action with informal English translation for BR PI0506780-4 with Search Report, Jul. 19, 2016.
CN Creative and Intellicig USA, CV11-6268 Invalidity Contentions, Apr. 12, 2012.
Collins, John M., Expert Report—Invalidity (Excerpts), CV14-01645, Jun. 18, 2015.
Collins, John M., Expert Report—Invalidity, CV14-01645—Appendix G—'331, Jun. 18, 2015.
Collins, John M., Expert Report—Invalidity, CV14-01645—Appendix H—'628, Jun. 18, 2015.
Collins, John M., Expert Report—Invalidity, CV14-01645—Appendix K-1—'726, Jun. 18, 2015.
Collins, John M., Expert Report—Invalidity, CV14-01645—Appendix K-2—'726, Jun. 18, 2015.
Collins, John M., Expert Report—Invalidity, CV14-01645—Appendix K-3—'726, Jun. 18, 2015.
Collins, John M., Expert Report—Invalidity, CV14-01645—Appendix K-4—'726, Jun. 18, 2015.
Collins, John M., Expert Report—Invalidity, CV14-01645—Appendix K-5—'726, Jun. 18, 2015.
Collins, John M., Expert Report—Invalidity, CV14-01645—Appendix K-6—'726, Jun. 18, 2015.
Cyphert Gil DBA NU1S, CV11-0367 Invalidity Contentions, Apr. 12, 2012.
R.J. Reynolds Vapor Company, Answer to Complaint in Fontem Holdings B.V. v. R.J. Reynolds Vapor Company, 16-CV-2286, Dkt. 027, Jun. 27, 2016.
R.J. Reynolds Vapor Company, First Amended Answer to Complaint in Fontem Holdings B.V. v. R.J. Reynolds Vapor Company, 16-CV-2286, Dkt. 033, Jul. 25, 2016.
State Intellectual Property Office, PRC China, Reexamination Decision on the Request for Invalidation for CN200420031182.0, Jun. 22, 2009 with English translation.
State Intellectual Property Office, PRC China, Search Report for PCT/CN2005/000337, Jul. 14, 2005.
United States Patent and Trademark Office Notice of Allowance for U.S. Appl. No. 13/560,789, dated May 10, 2013.
United States Patent and Trademark Office, Final Office Action for U.S. Appl. No. 12/944,123, dated Oct. 30, 2012.
United States Patent and Trademark Office, Final Office Action for U.S. Appl. No. 13/777,927, dated Jan. 16, 2014.
United States Patent and Trademark Office, Non-Final Office Action for U.S. Appl. No. 10/587,707, dated Sep. 1, 2009.
United States Patent and Trademark Office, Non-Final Office Action for U.S. Appl. No. 12/944,123, dated Dec. 13, 2011.
United States Patent and Trademark Office, Non-Final Office Action for U.S. Appl. No. 14/719,061, dated Jul. 8, 2015, 7 pgs.
United States Patent and Trademark Office, Non-Final Office Action for U.S. Appl. No. 14/719,923, dated Jan. 29, 2016, 6 pgs.
United States Patent and Trademark Office, Notice of Allowance for U.S. Appl. No. 14/719,061, dated Jan. 20, 2016, 7 pgs.
European Patent Office, Supplemental European Search Report for EP05729107, Jul. 31, 2007.
European Patent Office, Supplemental Partial European Search Reports for EP05729107, dated May 22, 2007.
Hewlett-Packard, Thermal Ink—Jet Print Cartridge Designers Guide (2nd Edition), Jan. 12, 1995.
Introduction to selecting and using electronic components, ISBN7-111-13752-3, exact publication date unknown, believed to be publically available at least as early as Jun. 2006.
IP Australia, Examiner's Report for AU 2005232354, dated Jan. 12, 2010.
IP Australia, Search and Examination Report for SG200604498-6, dated Apr. 16, 2008.
ITC Limited, Pre-Grant Opposition against IN3872/DELNP/2006, Aug. 11, 2014, 19 pgs.
Manual for Electric Engineers, 2nd Ed, Mar. 2000.
Manual for Mechanical Designers, 4th Ed, Jan. 2002.
Materials Manual—Nonmetal, Jul. 1, 1985.
Njoy, Inc. et al, Defendants' Joint Invalidity Contentions, CV14-01645 etc., Aug. 7, 2014 (see pp. 7-16).
Njoy, Inc. et al., Defendants' Joint Invalidity Contentions, CV14-01645 etc., Feb. 26, 2015 (see pp. 7-12).
Njoy, Inc. et al., Defendants' Joint Invalidity Contentions, CV-14-01645 etc., Attachment B—Claim Charts for U.S. Pat. No. 8,393,331, Aug. 7, 2014.
Njoy, Inc. et al., Defendants' Joint Invalidity Contentions, CV-14-01645 etc., Attachment C—Claim Charts for U.S. Pat. No. 8,490,628, Aug. 7, 2014.
Njoy, Inc. et al., Defendant's Joint Invalidity Contentions, CV14-01645 etc., Exhibit B—Claim Charts for U.S. Pat. No. 8,893,726—Feb. 26, 2015.
Nu Mark LLC, Answer and Counterclaims in Fontem Ventures B.V. v. Nu Mark LLC, 16-CV-1259, Dkt. 034, Oct. 26, 2016.
Nu Mark LLC, Answer to Complaint and Counterclaims in Fontem Ventures B.V. v. Nu Mark LLC, 16-CV-2291, Dkt. 025, Jun. 27, 2016.
Nu Mark LLC, First Amended Answer and Counterclaims in Fontem Ventures B.V. v. Nu Mark LLC, 16-CV-2291, Dkt. 042, Jul. 28, 2016.
R.J. Reynold Vapor Company, Answer to Complaint in Fontem Holdings B.V. v. R.J. Reynolds Vapor Company, 16-CV-3049, Dkt. 028, Jul. 25, 2016.
R.J. Reynolds Vapor Company, Preliminary Invalidity Contentions served in Fontem Ventures B.V. v. R.J. Reynolds Vapor Company, U.S. District Court for the Middle District of North Carolina, 16-cv-01255, Mar. 15, 2017.
R.J. Reynolds Vapor Company, Preliminary Invalidity Contentions, Exhibit B ('628 patent), 16-cv-01255, Mar. 15, 2017.
R.J. Reynolds Vapor Company, Preliminary Invalidity Contentions, Exhibit C ('726 patent), 16-cv-01255, Mar. 15, 2017.
R.J. Reynolds Vapor Company, Preliminary Invalidity Contentions, Exhibit F ('549 patent), 16-cv-01255, Mar. 15, 2017.
RJRV000000279-RJRV000000286, JP2001-291598 published Oct. 19, 2001, English Translation served with R.J. Reynolds Vapor Company's Preliminary Invalidity Contentions served Mar. 15, 2017.

(56) References Cited

OTHER PUBLICATIONS

RJRV000000446-RJRV000000464, US20040149282 by Hickle, published Aug. 5, 2004, served with R.J. Reynolds Vapor Company's Preliminary Invalidity Contentions served Mar. 15, 2017.
RJRV000016648-RJRV000016655, JPH9-326299 published Dec. 16, 1997, English Translation served with R.J. Reynolds Vapor Company's Preliminary Invalidity Contentions served Mar. 15, 2017.
RJRV000027018-RJRV000027024, U.S. Pat. No. 4,968,263 to Silbernagel, issued Nov. 6, 1990, served with R.J. Reynolds Vapor Company's Preliminary Invalidity Contentions served Mar. 15, 2017.
RJRV000027025-RJRV000027041, U.S. Pat. No. 5,266,746 to Nishihara, issued Nov. 30, 1993, served with R.J. Reynolds Vapor Company's Preliminary Invalidity Contentions served Mar. 15, 2017.
RJRV000039092-RJRV000039096, U.S. Pat. No. 3,685,522 to Kleinhans, issued Aug. 22, 1972, served with R.J. Reynolds Vapor Company's Preliminary Invalidity Contentions served Mar. 15, 2017.
RJRV000043203-RJRV00043214, U.S. Pat. No. 4,878,506 to Pinck, issued Nov. 7, 1989, served with R.J. Reynolds Vapor Company's Preliminary Invalidity Contentions served Mar. 15, 2017.
Sottera, Inc., CV11-0367 Invalidity Contentions, Apr. 12, 2012.
Sottera, Inc., Invalidity Contentions, Exhibit 7, CV11-0367, Apr. 12, 2012.
Sottera, Inc., Invalidity Contentions, Exhibit 8, CV11-0367, Apr. 12, 2012.
U.S. District Court, Central District of California, Western Division, Defendant Njoy. Inc.'s production documents Vlachos 0000061-72; Consolidated Case No. CV 14-01645 GW (MRW) and related consolidated cases, Jun. 4, 2015.
U.S. District Court, Central Di strict of California, Western Division, Defendant Njoy, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Memorandum of Points and Authorities in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 1 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 3 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 4 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy, Inc.'s Exhibit 5 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant Njoy. Inc.'s Reply Brief in Support of Defendants' Motion for Leave to Amend Invalidity Contentions dated Jul. 13, 2015 and filed in Consolidated Case No. CV 14-01645 GW (MRW) and related consolidated cases.
United States Patent and Trademark Office, Office Action for U.S. Appl. No. 13/777,927, dated Aug. 16, 2013.
Patent Trial and Appeal Board, United States Patent and Trademark Office, Inter Partes Review Institution Decision IPR2014-01289, Paper 8, Feb. 19, 2015.
Njoy, Inc., Petition for Inter Partes Review of U.S. Pat. No. 8,393,331—IPR2014-01289, Aug. 14, 2014.
Njoy, Inc., Petition for Inter Partes Review of U.S. Pat. No. 8,393,331—IPR2014-01289, Exhibit 1001 U.S. Pat. No. 8,393,331 ("The '331 patent"), Aug. 14, 2014.
Njoy, Inc., Petition for Inter Partes Review of U.S. Pat. No. 8,393,331—IPR2014-01289, Exhibit 1002 U.S. Pat. No. 8,393,331 File History ("File History"), Aug. 14, 2014.
Njoy, Inc., Petition for Inter Partes Review of U.S. Pat. No. 8,393,331—IPR2014-01289, Exhibit 1003 U.S. Pat. No. 6,155,268 ("Takeuchi"), Aug. 14, 2014.
Njoy, Inc., Petition for Inter Partes Review of U.S. Pat. No. 8,393,331—IPR2014-01289, Exhibit 1004 U.S. Pat. No. 6,234,167("Cox"), Aug. 14, 2014.
Njoy, Inc., Petition for Inter Partes Review of U.S. Pat. No. 8,393,331—IPR2014-01289, Exhibit 1005 U.S. Pat. No. 5,894,841 ("Voges"), Aug. 14, 2014.
Njoy, Inc., Petition for Inter Partes Review of U.S. Pat. No. 8,393,331—IPR2014-01289, Exhibit 1006 U.S. Pat. No. 4,990,939 ("Sekiya"), Aug. 14, 2014.
Njoy, Inc., Petition for Inter Partes Review of U.S. Pat. No. 8,393,331—IPR2014-01289, Exhibit 1007 U.S. Pat. No. 4,771,295 ("Baker"), Aug. 14, 2014.
Njoy, Inc., Petition for Inter Partes Review of U.S. Pat. No. 8,393,331—IPR2014-01289, Exhibit 1008 U.S. Pat. No. 5,743,251 ("Howell"), Aug. 14, 2014.
Njoy, Inc., Petition for Inter Partes Review of U.S. Pat. No. 8,393,331—IPR2014-01289, Exhibit 1009 U.S. Pat. No. 6,501,052 ("Cox '02"), Aug. 14, 2014.
Njoy, Inc., Petition for Inter Partes Review of U.S. Pat. No. 8,393,331—IPR2014-01289, Exhibit 1010 Thermal Ink—Jet Print Cartridge Designers Guide (2nd Edition Hewlett Packard) ("Jet Print Cartridge Designers Guide") Aug. 14, 2014.
Njoy, Inc., Petition for Inter Partes Review of U.S. Pat. No. 8,393,331—IPR2014-01289, Exhibit 1011 Collins Expert Declaration, Aug. 14, 2014.
Njoy, Inc., Petition for Inter Partes Review of U.S. Pat. No. 8,393,331—IPR2014-01289, Exhibit 1012 U.S. Pat. No. 3,747,120 ("Stemme"), Aug. 14, 2014.
Njoy, Inc., Petition for Inter Partes Review of U.S. Pat. No. 8,393,331—IPR2014-01289, Exhibit 1013 U.S. Pat. No. 4,797,692 ("Ims"), Aug. 14, 2014.
Njoy, Inc., Petition for Inter Partes Review of U.S. Pat. No. 8,393,331—IPR2014-01289, Exhibit 1014 U.S. Pat. No. 5,666,977 ("Higgins"), Aug. 14, 2014.
Njoy, Inc., Petition for Inter Partes Review of U.S. Pat. No. 8,393,331—IPR2014-01289, Exhibit 1015 U.S. Pat. No. 6,701,921 ("Sprinkel"), Aug. 14, 2014.
Njoy, Inc., Petition for Inter Partes Review of U.S. Pat. No. 8,393,331—IPR2014-01289, Exhibit 1016 U.S. Pat. No. 4,848,374 ("Chard"), Aug. 14, 2014.
Njoy, Inc., Petition for Inter Partes Review of U.S. Pat. No. 8,393,331—IPR2014-01289, Exhibit 1017 U.S. Pat. No. 5,060,671 ("Counts"), Aug. 14, 2014.
Njoy, Inc., Petition for Inter Partes Review of U.S. Pat. No. 8,393,331—IPR2014-01289, Exhibit 1018 European Patent No. 0,358,114 ("Brooks"), Aug. 14, 2014.
Njoy, Inc., Petition for Inter Partes Review of U.S. Pat. No. 8,393,331—IPR2014-01289, Exhibit 1019 International Publication No. WO 98/17131 ("Fleischhauer"), Aug. 14, 2014.
Njoy, Inc., Petition for Inter Partes Review of U.S. Pat. No. 8,393,331—IPR2014-01289, Exhibit 1020 U.S. Pat. No. 6,196,218 ("Voges II"), Aug. 14, 2014.

(56) References Cited

OTHER PUBLICATIONS

Njoy, Inc., Petition for Inter Partes Review of U.S. Pat. No. 8,393,331—IPR2014-01289, Exhibit 1021 U.S. Pat. No. 3,431,393 ("Katsuda"), Aug. 14, 2014.
Njoy, Inc., Petition for Inter Partes Review of U.S. Pat. No. 8,393,331—IPR2014-01289, Exhibit 1022 Certified English Translation of Chinese Publication No. CN1233436 ("Hongbin").
Njoy, Inc., Petition for Inter Partes Review of U.S. Pat. No. 8,393,331—IPR2014-01289, Exhibit 1023 U.S. Pat. No. 6,598,607 ("Adiga"), Aug. 14, 2014.
Njoy, Inc., Petition for Inter Partes Review of U.S. Pat. No. 8,393,331—IPR2014-01289, Exhibit 1024 U.S. Pat. No. 4,945,448 ("Bremenour"), Aug. 14, 2014.
Njoy, Inc., Petition for Inter Partes Review of U.S. Pat. No. 8,393,331—IPR2014-01289, Exhibit 1025 U.S. Pat. No. 2,057,353 ("Whittemore"), Aug. 14, 2014.
Njoy, Inc., Petition for Inter Partes Review of U.S. Pat. No. 8,393,331—IPR2014-01289, Exhibit 1026 Canadian Respiratory Journal Nov.-Dec. 1999;6(6), p. 509 ("Nicotine Microaerosol Inhaler"), Aug. 14, 2014.
Njoy, Inc., Petition for Inter Partes Review of U.S. Pat. No. 8,393,331—IPR2014-01289, Exhibit 1027 U.S. Pat. No. 6,471,782 ("Fang"), Aug. 14, 2014.
Njoy, Inc., Petition for Inter Partes Review of U.S. Pat. No. 8,393,331—IPR2014-01289, Exhibit 1028 International Publication No. WO 2003000324 A1 ("Karl"), Aug. 14, 2014.
Njoy, Inc., Petition for Inter Partes Review of U.S. Pat. No. 8,393,331—IPR2014-01289, Exhibit 1029 U.S. Pat. No. 6,062,213 ("Fuisz"), Aug. 14, 2014.
Njoy, Inc., Petition for Inter Partes Review of U.S. Pat. No. 8,393,331—IPR2014-01289, Exhibit 1030 International Publication No. WO 2002098390 A2 ("Hodges"), Aug. 14, 2014.
Njoy, Inc., Petition for Inter Partes Review of U.S. Pat. No. 8,393,331—IPR2014-01289, Exhibit 1031 U.S. Pat. No. 5,745,985 ("Ghosh"), Aug. 14, 2014.
Njoy, Inc., Petition for Inter Partes Review of U.S. Pat. No. 8,393,331—IPR2014-01289, Exhibit 1032 U.S. Pat. No. 4,676,237 ("Wood"), Aug. 14, 2014.
Njoy, Inc., Petition for Inter Partes Review of U.S. Pat. No. 8,393,331—IPR2014-01289, Exhibit 1033 U.S. Pat. No. 5,327,915 ("Porenski"), Aug. 14, 2014.
Njoy, Inc., Petition for Inter Partes Review of U.S. Pat. No. 8,393,331—IPR2014-01289, Exhibit 1034 U.S. Pat. No. 7,284,424 ("Kanke"), Aug. 14, 2014.
Njoy, Inc., Petition for Inter Partes Review of U.S. Pat. No. 8,393,331—IPR2014-01289, Exhibit 1035 U.S. Pat. No. 5,224,265 ("Dux"), Aug. 14, 2014.
Njoy, Inc., Petition for Inter Partes Review of U.S. Pat. No. 8,393,331—IPR2014-01289, Exhibit 1036 U.S. Pat. No. 6,620,659 ("Emmma"), Aug. 14, 2014.
Njoy, Inc., Petition for Inter Partes Review of U.S. Pat. No. 8,393,331—IPR2014-01289, Exhibit 1037 U.S. Pat. No. 3,400,998 ("Daugherty"), Aug. 14, 2014.
Njoy, Inc., Petition for Inter Partes Review of U.S. Pat. No. 8,393,331—IPR2014-01289, Exhibit 1038 European Patent Application No. EP0845220 B1 ("Susa"), Aug. 14, 2014.
Njoy, Inc., Petition for Inter Partes Review of U.S. Pat. No. 8,393,331—IPR2014-01289, Exhibit 1039 U.S. Pat. No. 5,703,633 ("Gehrer"), Aug. 14, 2014.
Njoy, Inc., Petition for Inter Partes Review of U.S. Pat. No. 8,393,331—IPR2014-01289, Exhibit 1040 U.S. Pat. No. 3,200,819 ("Gilbert"), Aug. 14, 2014.
Njoy, Inc., Petition for Inter Partes Review of U.S. Pat. No. 8,393,331—IPR2014-01289, Exhibit 1041 U.S. Pat. No. 3,502,588 ("Winberg"), Aug. 14, 2014.
Njoy, Inc., Petition for Inter Partes Review of U.S. Pat. No. 8,393,331—IPR2014-01289, Exhibit 1042 U.S. Pat. No. 3,203,025 ("Schreur"), Aug. 14, 2014.
Njoy, Inc., Petition for Inter Partes Review of U.S. Pat. No. 8,393,331—IPR2014-01289, Exhibit 1043 U.S. Pat. No. 4,945,929 ("Egilmex"), Aug. 14, 2014.
Njoy, Inc., Petition for Inter Partes Review of U.S. Pat. No. 8,393,331—IPR2014-01289, Exhibit 1044 U.S. Pat. No. 5,124,200 ("Mallonee"), Aug. 14, 2014.
Njoy, Inc., Petition for Inter Partes Review of U.S. Pat. No. 8,393,331—IPR2014-01289, Exhibit 1045 U.S. Patent App. Pub. No. 2006/0093977 A1 ("Pellizzari"), Aug. 14, 2014.
Njoy, Inc., Petition for Inter Partes Review of U.S. Pat. No. 8,393,331—IPR2014-01289, Exhibit 1046 U.S. Pat. No. 7,059,307 ("Pellizzari II"), Aug. 14, 2014.
Njoy, Inc., Petition for Inter Partes Review of U.S. Pat. No. 8,393,331—IPR2014-01289, Exhibit 1047 U.S. Pat. No. 5,996,589 ("St. Charles"), Aug. 14, 2014.
Njoy, Inc., Petition for Inter Partes Review of U.S. Pat. No. 8,393,331—IPR2014-01289, Exhibit 1048 U.S. Pat. No. 4,972,855 ("Kuriyama"), Aug. 14, 2014.
Njoy, Inc., Petition for Inter Partes Review of U.S. Pat. No. 8,393,331—IPR2014-01289, Exhibit 1049 Declaration of Dr. Saurabh Gupta, Aug. 14, 2014.
Patent Trial and Appeal Board, United States Patent and Trademark Office, Inter Partes Review Institution Decision IPR2014-01300, Paper 8, Feb. 19, 2015.
Njoy, Inc., Petition for Inter Partes Review of U.S. Pat. No. 8,490,628—IPR2014-01300, Aug. 15, 2014.
Njoy, Inc., Petition for Inter Partes Review of U.S. Pat. No. 8,490,628—IPR2014-01300, Exhibit 1001 U.S. Pat. No. 8,490,628 ("the '628 patent"), Aug. 15, 2014.
Njoy, Inc., Petition for Inter Partes Review of U.S. Pat. No. 8,490,628—IPR2014-01300, Exhibit 1002 U.S. Pat. No. 8,490,628 File History ("File History"), Aug. 15, 2014.
Njoy, Inc., Petition for Inter Partes Review of U.S. Pat. No. 8,490,628—IPR2014-01300, Exhibit 1003 U.S. Pat. No. 6,155,268 ("Takeuchi"), Aug. 15, 2014.
Njoy, Inc., Petition for Inter Partes Review of U.S. Pat. No. 8,490,628—IPR2014-01300, Exhibit 1004 U.S. Pat. No. 2,057,353 ("Whittemore"), Aug. 15, 2014.
Njoy, Inc., Petition for Inter Partes Review of U.S. Pat. No. 8,490,628—IPR2014-01300, Exhibit 1005 U.S. Pat. No. 7,143,766 ("Schuster"), Aug. 15, 2014.
Njoy, Inc., Petition for Inter Partes Review of U.S. Pat. No. 8,490,628—IPR2014-01300, Exhibit 1006 U.S. Pat. No. 5,996,589 ("St. Charles"), Aug. 15, 2014.
Njoy, Inc., Petition for Inter Partes Review of U.S. Pat. No. 8,490,628—IPR2014-01300, Exhibit 1007 U.S. Pat. No. 6,598,607 ("Adiga"), Aug. 15, 2014.
Njoy, Inc., Petition for Inter Partes Review of U.S. Pat. No. 8,490,628—IPR2014-01300, Exhibit 1008 European Patent Application No. EP0845220 B1 ("Susa"), Aug. 15, 2014.
Njoy, Inc., Petition for Inter Partes Review of U.S. Pat. No. 8,490,628—IPR2014-01300, Exhibit 1009 U.S. Pat. No. 3,200,819 ("Gilbert"), Aug. 15, 2014.
Njoy, Inc., Petition for Inter Partes Review of U.S. Pat. No. 8,490,628—IPR2014-01300, Exhibit 1010 U.S. Pat. No. 3,060,429 ("Winston"), Aug. 15, 2014.
Njoy, Inc., Petition for Inter Partes Review of U.S. Pat. No. 8,490,628—IPR2014-01300, Exhibit 1011 U.S. Pat. No. 5,894,841 ("Voges"), Aug. 15, 2014.
Njoy, Inc., Petition for Inter Partes Review of U.S. Pat. No. 8,490,628—IPR2014-01300, Exhibit 1012 U.S. Pat. No. 5,703,633 ("Gehrer"), Aug. 15, 2014.
Njoy, Inc., Petition for Inter Partes Review of U.S. Pat. No. 8,490,628—IPR2014-01300, Exhibit 1013 Thermal Ink—Jet Print Cartridge Designers Guide Edition (2nd Edition Hewlett Packard) ("Jet Print Cartridge Designers Guide"), Aug. 15, 2014.
Njoy, Inc., Petition for Inter Partes Review of U.S. Pat. No. 8,490,628—IPR2014-01300, Exhibit 1014 U.S. Pat. No. 5,666,977 ("Higgins"), Aug. 15, 2014.
Njoy, Inc., Petition for Inter Partes Review of U.S. Pat. No. 8,490,628—IPR2014-01300, Exhibit 1015 U.S. Pat. No. 6,701,921 ("Sprinkel"), Aug. 15, 2014.

(56) References Cited

OTHER PUBLICATIONS

Njoy, Inc., Petition for Inter Partes Review of U.S. Pat. No. 8,490,628—IPR2014-01300, Exhibit 1016 U.S. Pat. No. 4,848,374 ("Chard"), Aug. 15, 2014.
Njoy, Inc., Petition for Inter Partes Review of U.S. Pat. No. 8,490,628—IPR2014-01300, Exhibit 1017 U.S. Pat. No. 5,060,671 ("Counts"), Aug. 15, 2014.
Njoy, Inc., Petition for Inter Partes Review of U.S. Pat. No. 8,490,628—IPR2014-01300, Exhibit 1018 European U.S. Pat. No. 0,358,114 ("Brooks"), Aug. 15, 2014.
Njoy, Inc., Petition for Inter Partes Review of U.S. Pat. No. 8,490,628—IPR2014-01300, Exhibit 1019 International Publication No. WO 98/17131 ("Fleischhauer"), Aug. 15, 2014.
Njoy, Inc., Petition for Inter Partes Review of U.S. Pat. No. 8,490,628—IPR2014-01300, Exhibit 1020 U.S. Pat. No. 6,196,218 ("Voges II"), Aug. 15, 2014.
Njoy, Inc., Petition for Inter Partes Review of U.S. Pat. No. 8,490,628—IPR2014-01300, Exhibit 1021 U.S. Pat. No. 3,431,393 ("Katsuda"), Aug. 15, 2014.
Njoy, Inc., Petition for Inter Partes Review of U.S. Pat. No. 8,490,628—IPR2014-01300, Exhibit 1022 Certified English Translation of Chinese Publication No. CN1233436 ("Hongbin"), Aug. 15, 2014.
Njoy, Inc., Petition for Inter Partes Review of U.S. Pat. No. 8,490,628—IPR2014-01300, Exhibit 1023 Canadian Respiratory Journal Nov.-Dec. 1999;6(6), p. 509 ("Nicotine Microaerosol Inhaler"), Aug. 15, 2014.
Njoy, Inc., Petition for Inter Partes Review of U.S. Pat. No. 8,490,628—IPR2014-01300, Exhibit 1024 U.S. Pat. No. 4,972,855 ("Kuriyama"), Aug. 15, 2014.
Njoy, Inc., Petition for Inter Partes Review of U.S. Pat. No. 8,490,628—IPR2014-01300, Exhibit 1025 U.S. Pat. No. 6,322,268 ("Kaufman"), Aug. 15, 2014.
Njoy, Inc., Petition for Inter Partes Review of U.S. Pat. No. 8,490,628—IPR2014-01300, Exhibit 1026 U.S. Pat. No. 6,722,763 ("Hsu"), Aug. 15, 2014.
Njoy, Inc., Petition for Inter Partes Review of U.S. Pat. No. 8,490,628—IPR2014-01300, Exhibit 1027 U.S. Pat. No. 5,646,666 ("Cowger"), Aug. 15, 2014.
Njoy, Inc., Petition for Inter Partes Review of U.S. Pat. No. 8,490,628—IPR2014-01300, Exhibit 1028 U.S. Pat. No. 8,393,331 File History ("331 FileHistory"), Aug. 15, 2014.
Njoy, Inc., Petition for Inter Partes Review of U.S. Pat. No. 8,490,628—IPR2014-01300, Exhibit 1029 U.S. Pat. No. 4,945,448 ("Bremenour").
Njoy, Inc., Petition for Inter Partes Review of U.S. Pat. No. 8,490,628—IPR2014-01300, Exhibit 1030 U.S. Pat. No. 3,400,998 ("Daugherty"), Aug. 15, 2014.
Njoy, Inc., Petition for Inter Partes Review of U.S. Pat. No. 8,490,628—IPR2014-01300, Exhibit 1031 U.S. Pat. No. 5,745,985 ("Ghosh"), Aug. 15, 2014.
Njoy, Inc., Petition for Inter Partes Review of U.S. Pat. No. 8,490,628—IPR2014-01300, Exhibit 1032 U.S. Pat. No. 4,676,237 ("Wood"), Aug. 15, 2014.
Njoy, Inc., Petition for Inter Partes Review of U.S. Pat. No. 8,490,628—IPR2014-01300, Exhibit 1033 U.S. Pat. No. 5,327,915 ("Porenski"), Aug. 15, 2014.
Njoy, Inc., Petition for Inter Partes Review of U.S. Pat. No. 8,490,628—IPR2014-01300, Exhibit 1034 U.S. Pat. No. 7,284,424 ("Kanke"), Aug. 15, 2014.
Njoy, Inc., Petition for Inter Partes Review of U.S. Pat. No. 8,490,628—IPR2014-01300, Exhibit 1035 U.S. Pat. No. 5,224,265 ("Dux"), Aug. 15, 2014.
Njoy, Inc., Petition for Inter Partes Review of U.S. Pat. No. 8,490,628—IPR2014-01300, Exhibit 1036 U.S. Pat. No. 6,620,659 ("Emmma"), Aug. 15, 2014.
Njoy, Inc., Petition for Inter Partes Review of U.S. Pat. No. 8,490,628—IPR2014-01300, Exhibit 1037 U.S. Pat. No. 6,234,167("Cox"), Aug. 15, 2014.
Njoy, Inc., Petition for Inter Partes Review of U.S. Pat. No. 8,490,628—IPR2014-01300, Exhibit 1038 U.S. Pat. No. 4,990,939 ("Sekiya"), Aug. 15, 2014.
Njoy, Inc., Petition for Inter Partes Review of U.S. Pat. No. 8,490,628—IPR2014-01300, Exhibit 1039 U.S. Pat. No. 4,771,295 ("Baker"), Aug. 15, 2014.
Njoy, Inc., Petition for Inter Partes Review of U.S. Pat. No. 8,490,628—IPR2014-01300, Exhibit 1040—Collins Expert Declaration, Aug. 15, 2014.
Njoy, Inc., Petition for Inter Partes Review of U.S. Pat. No. 8,490,628—IPR2014-01300, Exhibit 1041 U.S. Pat. No. 5,743,251 ("Howell"), Aug. 15, 2014.
Njoy, Inc., Petition for Inter Partes Review of U.S. Pat. No. 8,490,628—IPR2014-01300, Exhibit 1042 U.S. Pat. No. 6,501,052 ("Cox '02"), Aug. 15, 2014.
Njoy, Inc., Petition for Inter Partes Review of U.S. Pat. No. 8,490,628—IPR2014-01300, Exhibit 1043 U.S. Pat. No. 4,797,692 ("Ims"), Aug. 15, 2014.
Njoy, Inc., Petition for Inter Partes Review of U.S. Pat. No. 8,490,628—IPR2014-01300, Exhibit 1044 U.S. Pat. No. 6,471,782 ("Fang"), Aug. 15, 2014.
Njoy, Inc., Petition for Inter Partes Review of U.S. Pat. No. 8,490,628—IPR2014-01300, Exhibit 1045 International Publication No. WO 2003000324 A1 ("Karl"), Aug. 15, 2014.
Njoy, Inc., Petition for Inter Partes Review of U.S. Pat. No. 8,490,628—IPR2014-01300, Exhibit 1046 International Publication No. WO 2002098390 A2 ("Hodges"), Aug. 15, 2014.
Njoy, Inc., Petition for Inter Partes Review of U.S. Pat. No. 8,490,628—IPR2014-01300, Exhibit 1047 U.S. Pat. No. 6,062,213 ("Fuisz"), Aug. 15, 2014.
Njoy, Inc., Petition for Inter Partes Review of U.S. Pat. No. 8,490,628—IPR2014-01300, Exhibit 1048 U.S. Appl. No. 2006/0,093,977 A1 ("Pellizzari"), Aug. 15, 2014.
Njoy, Inc., Petition for Inter Partes Review of U.S. Pat. No. 8,490,628—IPR2014-01300, Exhibit 1049 U.S. Pat. No. 7,059,307 B2 ("Pellizzari II"), Aug. 15, 2014.
Njoy, Inc., Petition for Inter Partes Review of U.S. Pat. No. 8,490,628—IPR2014-01300, Exhibit 1050 U.S. Pat. No. 3,203,025 ("Schreur"), Aug. 15, 2014.
Njoy, Inc., Petition for Inter Partes Review of U.S. Pat. No. 8,490,628—IPR2014-01300, Exhibit 1051 U.S. Application Publication Patent No. 2001/0,026,788 ("Piskorz"), Aug. 15, 2014.
Njoy, Inc., Petition for Inter Partes Review of U.S. Pat. No. 8,490,628—IPR2014-01300, Exhibit 1052 U.S. Pat. No. 6,102,036 ("Slutsky"), Aug. 15, 2014.
Njoy, Inc., Petition for Inter Partes Review of U.S. Pat. No. 8,490,628—IPR2014-01300, Exhibit 1053 U.S. Pat. No. 3,502,588 ("Winberg"), Aug. 15, 2014.
Njoy, Inc., Petition for Inter Partes Review of U.S. Pat. No. 8,490,628—IPR2014-01300, Exhibit 1054 U.S. Pat. No. 4,945,929 ("Egilmex"), Aug. 15, 2014.
Njoy, Inc., Petition for Inter Partes Review of U.S. Pat. No. 8,490,628—IPR2014-01300, Exhibit 1055 U.S. Pat. No. 5,124,200 ("Mallonee"), Aug. 15, 2014.
Njoy, Inc., Petition for Inter Partes Review of U.S. Pat. No. 8,490,628—IPR2014-01300, Exhibit 1056 Declaration of Dr. Saurabh Gupta, Aug. 15, 2014.
Patent Trial and Appeal Board, United States Patent and Trademark Office, Inter Partes Review Institution Decision—Denying Institution of Inter Partes Review—IPR2015-01302, Paper 15, Dec. 15, 2015.
Njoy, Inc. et al., Petition for Inter Partes Review of U.S. Pat. No. 8,893,726—IPR2015-01302, May 29, 2015.
Njoy, Inc. et al., Petition for Inter Partes Review of U.S. Pat. No. 8,893,726—IPR2015-01302, Exhibit 1001 U.S. Pat. No. 8,893,726 ("the '726 patent"), May 29, 2015.
Njoy, Inc. et al., Petition for Inter Partes Review of U.S. Pat. No. 8,893,726—IPR2015-01302, Exhibit 1002—Nayfeh Expert Declaration, May 29, 2015.
Njoy, Inc. et al., Petition for Inter Partes Review of U.S. Pat. No. 8,893,726—IPR2015-01302, Exhibit 1003 U.S. Pat. No. 6,155,268 ("Takeuchi"), May 29, 2015.

(56) References Cited

OTHER PUBLICATIONS

Njoy, Inc. et al., Petition for Inter Partes Review of U.S. Pat. No. 8,893,726—IPR2015-01302, Exhibit 1004 U.S. Pat. No. 5,144,962 ("Counts"), May 29, 2015.
Njoy, Inc. et al., Petition for Inter Partes Review of U.S. Pat. No. 8,893,726—IPR2015-01302, Exhibit 1005 U.S. Pat. No. 6,322,268 ("Kaufmann"), May 29, 2015.
Njoy, Inc. et al., Petition for Inter Partes Review of U.S. Pat. No. 8,893,726—IPR2015-01302, Exhibit 1006 '726 Patent File History, Non-Final Rejection (Aug. 16, 2013), May 29, 2015.
Njoy, Inc. et al., Petition for Inter Partes Review of U.S. Pat. No. 8,893,726—IPR2015-01302, Exhibit 1007 '726 Patent File History, Notice of Allowance (Aug. 18, 2014), May 29, 2015.
Njoy, Inc. et al., Petition for Inter Partes Review of U.S. Pat. No. 8,893,726—IPR2015-01302, Exhibit 1008 '726 Patent File History, Collected Info. Disclosure Statements, May 29, 2015.
Njoy, Inc. et al., Petition for Inter Partes Review of U.S. Pat. No. 8,893,726—IPR2015-01302, Exhibit 1009 Markman Hearing/Claim Construction Order, Fontem Ventures, B.V. v. Njoy, Inc., No. 14-cv-1645, Dkt. 133 (C.D. Cal. May 7, 2015), May 29, 2015.
Njoy, Inc. et al., Petition for Inter Partes Review of U.S. Pat. No. 8,893,726—IPR2015-01302, Exhibit 1010 Rulings on Claim Construction, Fontem Ventures, B.V. v. Njoy, Inc., No. 14-cv-1645, Dkt. 65 (C.D. Cal. Jan. 29, 2015), May 29, 2015.
Njoy, Inc. et al., Petition for Inter Partes Review of U.S. Pat. No. 8,893,726—IPR2015-01302, Exhibit 1011 Joint Claim Construction and Prehearing Statement, Fontem Ventures, B.V. v. Njoy, Inc., No. 14-cv-1645, Dkt. 93 (C.D. Cal. Mar. 19, 2015), May 29, 2015.
Njoy, Inc. et al., Petition for Inter Partes Review of U.S. Pat. No. 8,893,726—IPR2015-01302, Exhibit 1012 Revised Joint Claim Construction and Prehearing Statement, Fontem Ventures, B.V. v. Njoy, Inc., No. 14-cv-1645, Dkt. 34 (C.D. Cal. Sep. 30, 2014), May 29, 2015.
Njoy, Inc. et al., Petition for Inter Partes Review of U.S. Pat. No. 8,893,726—IPR2015-01302, Exhibit 1013 U.S. Pat. No. 4,945,931 ("the '931 patent"), May 29, 2015.
Njoy, Inc. et al., Petition for Inter Partes Review of U.S. Pat. No. 8,893,726—IPR2015-01302, Exhibit 1014 Curriculum Vitae of Samir Nayfeh, Ph.D., May 29, 2015.
USPTO PTAB, R.J. Reynolds Vapor Co. v. Fontem Holdings 1 B.V., IPR2016-01270, Paper 11, Decision Denying Inter Partes Review, dated Jan. 4, 2017.
R.J. Reynolds Vapor Company, Petition for Inter Partes Review of U.S. Pat. No. 8,893,726—IPR2016-01270, Paper 2, Jul. 2, 2016.
R.J. Reynolds Vapor Company, Petition for Inter Partes Review of U.S. Pat. No. 8,893,726—IPR2016-01270, Ex. 1001 U.S. Pat. No. 8,893,726 ("'726 Patent"), Jul. 2, 2016.
R.J. Reynolds Vapor Company, Petition for Inter Partes Review of U.S. Pat. No. 8,893,726—IPR2016-01270, Ex. 1002 '726 Patent File History, Non-Final Rejection (Aug. 16, 2013) ("Non-Final Rejection"), Jul. 2, 2016.
R.J. Reynolds Vapor Company, Petition for Inter Partes Review of U.S. Pat. No. 8,893,726—IPR2016-01270, Ex. 1003 '726 Patent File History, Amendment (Oct. 8, 2013) ("Amendment"), Jul. 2, 2016.
R.J. Reynolds Vapor Company, Petition for Inter Partes Review of U.S. Pat. No. 8,893,726—IPR2016-01270, Ex. 1004 '726 Patent File History, Notice of Allowance (Aug. 18, 2014), Jul. 2, 2016.
R.J. Reynolds Vapor Company, Petition for Inter Partes Review of U.S. Pat. No. 8,893,726—IPR2016-01270, Ex. 1005 Njoy, Inc. v. Fontem Holdings 1 B.V., IPR2015-01302 (PTAB, filed May 29, 2015), Paper No. 15 ("Prior Decision"), Jul. 2, 2016.
R.J. Reynolds Vapor Company, Petition for Inter Partes Review of U.S. Pat. No. 8,893,726—IPR2016-01270, Ex. 1006 U.S. Pat. No. 4,947,874 ("Brooks"), Jul. 2, 2016.
R.J. Reynolds Vapor Company, Petition for Inter Partes Review of U.S. Pat. No. 8,893,726—IPR2016-01270, Ex. 1007 U.S. Pat. No. 5,944,025 ("Cook"), Jul. 2, 2016.
R.J. Reynolds Vapor Company, Petition for Inter Partes Review of U.S. Pat. No. 8,893,726—IPR2016-01270, Ex. 1008 U.S. Pat. No. 6,155,268 ("Takeuchi"), Jul. 2, 2016.
R.J. Reynolds Vapor Company, Petition for Inter Partes Review of U.S. Pat. No. 8,893,726—IPR2016-01270, Ex. 1009 Declaration of Robert Sturges, Ph.D. ("Sturges Decl."), Jul. 2, 2016.
R.J. Reynolds Vapor Company, Petition for Inter Partes Review of U.S. Pat. No. 8,893,726—IPR2016-01270, Ex. 1010 Njoy, Inc. v. Fontem Holdings 1 B.V., IPR2015-01302 (PTAB, filed May 29, 2015), Paper No. 2 ("Njoy Petition"), Jul. 2, 2016.
R.J. Reynolds Vapor Company, Petition for Inter Partes Review of U.S. Pat. No. 8,893,726—IPR2016-01270, Ex. 1011 Njoy, Inc. v. Fontem Holdings 1 B.V., IPR2015-01302 (PTAB, filed May 29, 2015), Paper No. 6 ("Patent Owner Preliminary Response"), Jul. 2, 2016.
R.J. Reynolds Vapor Company, Petition for Inter Partes Review of U.S. Pat. No. 8,893,726—IPR2016-01270, Ex. 1012 U.S. Pat. No. 5,703,633 ("Gehrer"), Jul. 2, 2016.
USPTO Patent Trial and Appeal Board, *Nu Mark LLC v. Fontem Holdings 1 B.V.*, IPT2016-01283, Paper 12, Decision Denying Inter Partes Review, Nov. 30, 2016.
Nu Mark LLC, Petition for Inter Partes Review of U.S. Pat. No. 8,490,628—IPR2016-01283, Paper 1, Jun. 28, 2016.
Nu Mark LLC, Petition for Inter Partes Review of U.S. Pat. No. 8,490,628—IPR2016-01283, Ex. 1101 U.S. Pat. No. 8,490,628 (the "628 Patent"), Jun. 28, 2016.
Nu Mark LLC, Petition for Inter Partes Review of U.S. Pat. No. 8,490,628—IPR2016-01283, Ex. 1102 File History for U.S. Pat. No. 8,490,628, Jun. 28, 2016.
Nu Mark LLC, Petition for Inter Partes Review of U.S. Pat. No. 8,490,628—IPR2016-01283, Ex. 1103 Declaration of John M. Collins, Ph.D., Jun. 28, 2016.
Nu Mark LLC, Petition for Inter Partes Review of U.S. Pat. No. 8,490,628—IPR2016-01283, Ex. 1104 Curriculum Vitae of Dr. John M. Collins, Jun. 28, 2016.
Nu Mark LLC, Petition for Inter Partes Review of U.S. Pat. No. 8,490,628—IPR2016-01283, Ex. 1105 U.S. Pat. App. Pub. No. 2007/0267031 A1 ("Hon 031"), Jun. 28, 2016.
Nu Mark LLC, Petition for Inter Partes Review of U.S. Pat. No. 8,490,628—IPR2016-01283, Ex. 1106 File History for U.S. Appl. No. 12/944,123 (now U.S. Pat. No. 8,393,331), Jun. 28, 2016.
Nu Mark LLC, Petition for Inter Partes Review of U.S. Pat. No. 8,490,628—IPR2016-01283, Ex. 1107 Substitute Specification filed in U.S. Appl. No. 12/944,123 (now U.S. Pat. No. 8,393,331), Jun. 28, 2016.
Nu Mark LLC, Petition for Inter Partes Review of U.S. Pat. No. 8,490,628—IPR2016-01283, Ex. 1108 File History for U.S. Appl. No. 10/587,707 (now U.S. Pat. No. 7,832,410), Jun. 28, 2016.
Nu Mark LLC, Petition for Inter Partes Review of U.S. Pat. No. 8,490,628—IPR2016-01283, Ex. 1109 Certified Translation of CN 20040031182, Jun. 28, 2016.
Nu Mark LLC, Petition for Inter Partes Review of U.S. Pat. No. 8,490,628—IPR2016-01283, Ex. 1110 Decision Instituting Inter Partes Review—IPR2014-01300, Jun. 28, 2016.
Nu Mark LLC, Petition for Inter Partes Review of U.S. Pat. No. 8,490,628—IPR2016-01283, Ex. 1111 Claim Construction Order, Jan. 29, 2015, Jun. 28, 2016.
Nu Mark LLC, Petition for Inter Partes Review of U.S. Pat. No. 8,490,628—IPR2016-01283, Ex.1112 U.S. Pat. No. 7,832,410 (the "410 Patent"), Jun. 28, 2016.
Nu Mark LLC, Petition for Inter Partes Review of U.S. Pat. No. 8,490,628—IPR2016-01283, Ex.1113 U.S. Pat. No. 8,689,805 (the "805 Patent"), Jun. 28, 2016.
Nu Mark LLC, Petition for Inter Partes Review of U.S. Pat. No. 8,490,628—IPR2016-01283, Ex.1114 File History for U.S. Appl. No. 13/426,817 (issued as U.S. Pat. No. 8,689,805), Jun. 28, 2016.
Nu Mark LLC, Petition for Inter Partes Review of U.S. Pat. No. 8,490,628—IPR2016-01283, Ex.1115 EP 1736065 A1, Jun. 28, 2016.
Nu Mark LLC, Petition for Inter Partes Review of U.S. Pat. No. 8,490,628—IPR2016-01283, Ex.1116 Complaint, Fontem Ventures B.V., et al. v. Nu Mark LLC, Case No. 2:16-cv-02291, Jun. 28, 2016.

(56) References Cited

OTHER PUBLICATIONS

Nu Mark LLC, Petition for Inter Partes Review of U.S. Pat. No. 8,490,628—IPR2016-01283, Ex.1117 Certified Translation of WO 2005/099494, Jun. 28, 2016.
Nu Mark LLC, Petition for Inter Partes Review of U.S. Pat. No. 8,490,628—IPR2016-01283, Ex.1118 WO 2005/099494 Chinese version with English abstract (face), Jun. 28, 2016.
USPTO PTAB, *Nu Mark LLC v. Fontem Holdings 1 B.V.*, IPR2016-01285, Paper 10, Decision Denying Inter Partes Review, Nov. 30, 2016.
Nu Mark LLC, Petition for Inter Partes Review of U.S. Pat. No. 8,490,628—IPR2016-01285, Paper 2, Jun. 28, 2016.
Nu Mark LLC, Petition for Inter Partes Review of U.S. Pat. No. 8,490,628—IPR2016-01285, Ex.1001 U.S. Pat. No. 8,490,628 ("the 628 Patent"), Jun. 28, 2016.
Nu Mark LLC, Petition for Inter Partes Review of U.S. Pat. No. 8,490,628—IPR2016-01285, Ex.1002 File History for U.S. Pat. No. 8,490,628, Jun. 28, 2016.
Nu Mark LLC, Petition for Inter Partes Review of U.S. Pat. No. 8,490,628—IPR2016-01285, Ex.1003 Declaration of John M. Collins, Ph.D. ("Collins Decl."), Jun. 28, 2016.
Nu Mark LLC, Petition for Inter Partes Review of U.S. Pat. No. 8,490,628—IPR2016-01285, Ex.1004 U.S. Pat. No. 6,155,268 ("Takeuchi"), Jun. 28, 2016.
Nu Mark LLC, Petition for Inter Partes Review of U.S. Pat. No. 8,490,628—IPR2016-01285, Ex.1005 U.S. Pat. No. 2,057,353 ("Whittemore"), Jun. 28, 2016.
Nu Mark LLC, Petition for Inter Partes Review of U.S. Pat. No. 8,490,628—IPR2016-01285, Ex.1006 Decision—Institution of Inter Partes Review, Case No. IPR2014-01300 ("628 Decision"), Jun. 28, 2016.
Nu Mark LLC, Petition for Inter Partes Review of U.S. Pat. No. 8,490,628—IPR2016-01285, Ex.1007 File History for U.S. Pat. No. 8,393,331, Jun. 28, 2016.
Nu Mark LLC, Petition for Inter Partes Review of U.S. Pat. No. 8,490,628—IPR2016-01285, Ex.1008 Order to Terminate Proceedings, Case No. IPR2014-01300, Jun. 28, 2016.
Nu Mark LLC, Petition for Inter Partes Review of U.S. Pat. No. 8,490,628—IPR2016-01285, Ex.1009 U.S. Pat. No. 5,743,251 ("Howell"), Jun. 28, 2016.
Nu Mark LLC, Petition for Inter Partes Review of U.S. Pat. No. 8,490,628—IPR2016-01285, Ex.1010 U.S. Pat. No. 6,598,607 ("Adiga"), Jun. 28, 2016.
Nu Mark LLC, Petition for Inter Partes Review of U.S. Pat. No. 8,490,628—IPR2016-01285, Ex.1011 U.S. Pat. No. 5,894,841 ("Voges"), Jun. 28, 2016.
Nu Mark LLC, Petition for Inter Partes Review of U.S. Pat. No. 8,490,628—IPR2016-01285, Ex.1012 U.S. Pat. No. 6,322,268 ("Kaufman"), Jun. 28, 2016.
Nu Mark LLC, Petition for Inter Partes Review of U.S. Pat. No. 8,490,628—IPR2016-01285, Ex.1013 U.S. Pat. No. 4,771,295 ("Baker"), Jun. 28, 2016.
Nu Mark LLC, Petition for Inter Partes Review of U.S. Pat. No. 8,490,628—IPR2016-01285, Ex.1014 U.S. Pat. No. 5,703,633 ("Gehrer"), Jun. 28, 2016.
Nu Mark LLC, Petition for Inter Partes Review of U.S. Pat. No. 8,490,628—IPR2016-01285, Ex.1015 U.S. Pat. No. 5,124,200 ("Mallonee"), Jun. 28, 2016.
Nu Mark LLC, Petition for Inter Partes Review of U.S. Pat. No. 8,490,628—IPR2016-01285, Ex.1016 U.S. Pat. No. 4,797,692 ("Ims"), Jun. 28, 2016.
Nu Mark LLC, Petition for Inter Partes Review of U.S. Pat. No. 8,490,628—IPR2016-01285, Ex.1017 Thermal Ink-Jet Print Cartridge Designers Guide ("Ink-Jet Guide"), Jun. 28, 2016.
Nu Mark LLC, Petition for Inter Partes Review of U.S. Patent Pub. No. 8,490,628—IPR2016-01285, Ex.1018 U.S. Pat. No. 2006/0093977 ("Pellizzari I"), Jun. 28, 2016.
Nu Mark LLC, Petition for Inter Partes Review of U.S. Pat. No. 8,490,628—IPR2016-01285, Ex.1019 U.S. Pat. No. 7,059,307 ("Pellizzari II"), Jun. 28, 2016.

Nu Mark LLC, Petition for Inter Partes Review of U.S. Pat. No. 8,490,628—IPR2016-01285, Ex.1020 U.S. Pat. No. 6,501,052 ("Cox II"), Jun. 28, 2016.
Nu Mark LLC, Petition for Inter Partes Review of U.S. Pat. No. 8,490,628—IPR2016-01285, Ex.1021 U.S. Pat. No. 6,234,167 ("Cox"), Jun. 28, 2016.
Nu Mark LLC, Petition for Inter Partes Review of U.S. Pat. No. 8,490,628—IPR2016-01285, Ex.1022 U.S. Pat. No. 5,666,977 ("Higgins"), Jun. 28, 2016.
Nu Mark LLC, Petition for Inter Partes Review of U.S. Pat. No. 8,490,628—IPR2016-01285, Ex.1023 European Patent Application No. 0358114 A2 ("Brooks 114"), Jun. 28, 2016.
Nu Mark LLC, Petition for Inter Partes Review of U.S. Pat. No. 8,490,628—IPR2016-01285, Ex.1024 U.S. Pat. No. 7,284,424 ("Kanke"), Jun. 28, 2016.
Nu Mark LLC, Petition for Inter Partes Review of U.S. Pat. No. 8,490,628—IPR2016-01285, Ex.1025 U.S. Pat. No. 5,224,265 ("Dux"), Jun. 28, 2016.
Nu Mark LLC, Petition for Inter Partes Review of U.S. Pat. No. 8,490,628—IPR2016-01285, Ex.1026 U.S. Pat. No. 6,620,659 ("Emmma"), Jun. 28, 2016.
Nu Mark LLC, Petition for Inter Partes Review of U.S. Pat. No. 8,490,628—IPR2016-01285, Ex.1027 U.S. Pat. No. 5,745,985 ("Ghosh"), Jun. 28, 2016.
Nu Mark LLC, Petition for Inter Partes Review of U.S. Pat. No. 8,490,628—IPR2016-01285, Ex.1028 U.S. Pat. No. 4,676,237 ("Wood"), Jun. 28, 2016.
Nu Mark LLC, Petition for Inter Partes Review of U.S. Pat. No. 8,490,628—IPR2016-01285, Ex.1029 U.S. Pat. No. 4,945,448 ("Bremenour"), Jun. 28, 2016.
Nu Mark LLC, Petition for Inter Partes Review of U.S. Pat. No. 8,490,628—IPR2016-01285, Ex.1030 Certified Translation of Chinese Utility Model Publication No. CN 1233436A ("Hongbin"), Jun. 28, 2016.
Nu Mark LLC, Petition for Inter Partes Review of U.S. Pat. No. 8,490,628—IPR2016-01285, Ex.1031 U.S. Pat. No. 6,196,218 ("Voges II"), Jun. 28, 2016.
Nu Mark LLC, Petition for Inter Partes Review of U.S. Pat. No. 8,490,628—IPR2016-01285, Ex.1032 U.S. Pat. No. 6,722,763 ("Hsu"), Jun. 28, 2016.
Nu Mark LLC, Petition for Inter Partes Review of U.S. Pat. No. 8,490,628—IPR2016-01285, Ex.1033 U.S. Pat. No. 4,947,875 ("Brooks 875"), Jun. 28, 2016.
Nu Mark LLC, Petition for Inter Partes Review of U.S. Pat. No. 8,490,628—IPR2016-01285, Ex.1034 U.S. Pat. No. 5,646,666 ("Cowger"), Jun. 28, 2016.
Nu Mark LLC, Petition for Inter Partes Review of U.S. Pat. No. 8,490,628—IPR2016-01285, Ex.1035 U.S. Pat. No. 1,514,682 ("Wilson"), Jun. 28, 2016.
Nu Mark LLC, Petition for Inter Partes Review of U.S. Pat. No. 8,490,628—IPR2016-01285, Ex.1036 U.S. Pat. No. 3,200,819 ("Gilbert"), Jun. 28, 2016.
Nu Mark LLC, Petition for Inter Partes Review of U.S. Pat. No. 8,490,628—IPR2016-01285, Ex.1037 U.S. Pat. No. 6,491,233 ("Nichols"), Jun. 28, 2016.
Nu Mark LLC, Petition for Inter Partes Review of U.S. Pat. No. 8,893,726—IPR2016-01288, Paper 1, Jun. 28, 2016.
Nu Mark LLC, Petition for Inter Partes Review of U.S. Pat. No. 8,893,726—IPR2016-01288, Ex.1101 U.S. Pat. No. 8,893,726 (the "726 Patent"), Jun. 28, 2016.
Nu Mark LLC, Petition for Inter Partes Review of U.S. Pat. No. 8,893,726—IPR2016-01288, Ex.1102 File History for U.S. Pat. No. 8,893,726, Jun. 28, 2016.
Nu Mark LLC, Petition for Inter Partes Review of U.S. Pat. No. 8,893,726—IPR2016-01288, Ex.1103 Declaration of John M. Collins, Ph.D., Jun. 28, 2016.
Nu Mark LLC, Petition for Inter Partes Review of U.S. Pat. No. 8,893,726—IPR2016-01288, Ex.1104 Curriculum Vitae of Dr. John M. Collins, Jun. 28, 2016.
Nu Mark LLC, Petition for Inter Partes Review of U.S. Pat. No. 8,893,726—IPR2016-01288, Ex.1105 U.S. Appl. No. 2007/0267031 A1 ("Hon 031"), Jun. 28, 2016.

(56) References Cited

OTHER PUBLICATIONS

Nu Mark LLC, Petition for Inter Partes Review of U.S. Pat. No. 8,893,726—IPR2016-01288, Ex.1106 File History for U.S. Appl. No. 12/944,123 (now U.S. Pat. No. 8,393,331), Jun. 28, 2016.
Nu Mark LLC, Petition for Inter Partes Review of U.S. Pat. No. 8,893,726—IPR2016-01288, Ex.1107 Substitute Specification filed in U.S. Appl. No. 12/944,123 (now U.S. Pat. No. 8,393,331), Jun. 28, 2016.
Nu Mark LLC, Petition for Inter Partes Review of U.S. Pat. No. 8,893,726—IPR2016-01288, Ex.1108 File History for U.S. Appl. No. 10/587,707 (now U.S. Pat. No. 7,832,410), Jun. 28, 2016.
Nu Mark LLC, Petition for Inter Partes Review of U.S. Pat. No. 8,893,726—IPR2016-01288, Ex.1109 Certified Translation of CN 20040031182, Jun. 28, 2016.
Nu Mark LLC, Petition for Inter Partes Review of U.S. Pat. No. 8,893,726—IPR2016-01288, Ex.1110 Decision Denying Inter Partes Review—IPR2014-01302, Jun. 28, 2016.
Nu Mark LLC, Petition for Inter Partes Review of U.S. Pat. No. 8,893,726—IPR2016-01288, Ex.1112 U.S. Pat. No. 7,832,410 (the "410 Patent"), Jun. 28, 2016.
Nu Mark LLC, Petition for Inter Partes Review of U.S. Pat. No. 8,893,726—IPR2016-01288, Ex.1113 U.S. Pat. No. 8,689,805 (the "805 Patent"), Jun. 28, 2016.
Nu Mark LLC, Petition for Inter Partes Review of U.S. Pat. No. 8,893,726—IPR2016-01288, Ex.1114 File History for U.S. Appl. No. 13/426,817 (now U.S. Pat. No. 8,689,805), Jun. 28, 2016.
Nu Mark LLC, Petition for Inter Partes Review of U.S. Pat. No. 8,893,726—IPR2016-01288, Ex.1115 EP 1736065 A1, Jun. 28, 2016.
Nu Mark LLC, Petition for Inter Partes Review of U.S. Pat. No. 8,893,726—IPR2016-01288, Ex.1116 Complaint, *Fontem Ventures B.V., et al.* v. *Nu Mark LLC*, Case No. 2:16-cv-02291 (excerpts), Jun. 28, 2016.
Nu Mark LLC, Petition for Inter Partes Review of U.S. Pat. No. 8,893,726—IPR2016-01288, Ex.1117 Certified Translation of WO 2005/099494, Jun. 28, 2016.
Nu Mark LLC, Petition for Inter Partes Review of U.S. Pat. No. 8,893,726—IPR2016-01288, Ex.1118 WO 2005/099494 Chinese version with English abstract (face), Jun. 28, 2016.
Nu Mark LLC, Petition for Inter Partes Review of U.S. Pat. No. 8,893,726—IPR2016-01297, Paper 1, Jun. 28, 2016.
Nu Mark LLC, Petition for Inter Partes Review of U.S. Pat. No. 8,893,726—IPR2016-01297, Ex.1001 U.S. Pat. No. 8,893,726 ("the 726 Patent"), Jun. 28, 2016.
Nu Mark LLC, Petition for Inter Partes Review of U.S. Pat. No. 8,893,726—IPR2016-01297, Ex.1002 File History for U.S. Pat. No. 8,893,726, Jun. 28, 2016.
Nu Mark LLC, Petition for Inter Partes Review of U.S. Pat. No. 8,893,726—IPR2016-01297, Ex.1003 Declaration of John M. Collins, Ph.D., Jun. 28, 2016.
Nu Mark LLC, Petition for Inter Partes Review of U.S. Pat. No. 8,893,726—IPR2016-01297, Ex.1004 U.S. Pat. No. 6,155,268 ("Takeuchi"), Jun. 28, 2016.
Nu Mark LLC, Petition for Inter Partes Review of U.S. Pat. No. 8,893,726—IPR2016-01297, Ex.1005 U.S. Pat. No. 2,057,353 ("Whittemore"), Jun. 28, 2016.
Nu Mark LLC, Petition for Inter Partes Review of U.S. Pat. No. 8,893,726—IPR2016-01297, Ex.1006 Decision—Institution of Inter Partes Review, Case No. IPR2014-01300 ("628 Decision"), Jun. 28, 2016.
Nu Mark LLC, Petition for Inter Partes Review of U.S. Pat. No. 8,893,726—IPR2016-01297, Ex.1007 Decision—Institution of Inter Partes Review, Case No. IPR2014-01289 ("331 Decision"), Jun. 28, 2016.
Nu Mark LLC, Petition for Inter Partes Review of U.S. Pat. No. 8,893,726—IPR2016-01297, Ex.1008 U.S. Pat. No. 1,514,682 ("Wilson"), Jun. 28, 2016.
Nu Mark LLC, Petition for Inter Partes Review of U.S. Pat. No. 8,893,726—IPR2016-01297, Ex.1009 U.S. Pat. No. 5,743,251 ("Howell"), Jun. 28, 2016.
Nu Mark LLC, Petition for Inter Partes Review of U.S. Pat. No. 8,893,726—IPR2016-01297, Ex.1010 U.S. Pat. No. 6,598,607 ("Adiga"), Jun. 28, 2016.
Nu Mark LLC, Petition for Inter Partes Review of U.S. Pat. No. 8,893,726—IPR2016-01297, Ex.1011 U.S. Pat. No. 5,894,841 ("Voges"), Jun. 28, 2016.
Nu Mark LLC, Petition for Inter Partes Review of U.S. Pat. No. 8,893,726—IPR2016-01297, Ex.1012 U.S. Pat. No. 4,990,939 ("Sekiya"), Jun. 28, 2016.
Nu Mark LLC, Petition for Inter Partes Review of U.S. Pat. No. 8,893,726—IPR2016-01297, Ex.1013 U.S. Pat. No. 4,771,295 ("Baker"), Jun. 28, 2016.
Nu Mark LLC, Petition for Inter Partes Review of U.S. Pat. No. 8,893,726—IPR2016-01297, Ex.1014 U.S. Pat. No. 5,703,633 ("Gehrer"), Jun. 28, 2016.
Nu Mark LLC, Petition for Inter Partes Review of U.S. Pat. No. 8,893,726—IPR2016-01297, Ex.1015 U.S. Pat. No. 5,124,200 ("Mallonee"), Jun. 28, 2016.
Nu Mark LLC, Petition for Inter Partes Review of U.S. Pat. No. 8,893,726—IPR2016-01297, Ex.1016 U.S. Pat. No. 4,797,692 ("Ims"), Jun. 28, 2016.
Nu Mark LLC, Petition for Inter Partes Review of U.S. Pat. No. 8,893,726—IPR2016-01297, Ex.1017 U.S. Pat. No. 3,200,819 ("Gilbert"), Jun. 28, 2016.
Nu Mark LLC, Petition for Inter Partes Review of U.S. Pat. No. 8,893,726—IPR2016-01297, Ex.1018 U.S. Patent Application No. 2006/0093977 A1 ("Pellizzari I"), Jun. 28, 2016.
Nu Mark LLC, Petition for Inter Partes Review of U.S. Pat. No. 8,893,726—IPR2016-01297, Ex.1019 U.S. Pat. No. 7,059,307 ("Pellizzari II"), Jun. 28, 2016.
Nu Mark LLC, Petition for Inter Partes Review of U.S. Pat. No. 8,893,726—IPR2016-01297, Ex.1020 U.S. Pat. No. 6,501,052 ("Cox II"), Jun. 28, 2016.
Nu Mark LLC, Petition for Inter Partes Review of U.S. Pat. No. 8,893,726—IPR2016-01297, Ex.1021 U.S. Pat. No. 6,234,167 ("Cox"), Jun. 28, 2016.
Nu Mark LLC, Petition for Inter Partes Review of U.S. Pat. No. 8,893,726—IPR2016-01297, Ex.1022 U.S. Pat. No. 5,666,977 ("Higgins"), Jun. 28, 2016.
Nu Mark LLC, Petition for Inter Partes Review of U.S. Pat. No. 8,893,726—IPR2016-01297, Ex.1023 European Patent Application No. 0358114 A2 ("Brooks 114"), Jun. 28, 2016.
Nu Mark LLC, Petition for Inter Partes Review of U.S. Pat. No. 8,893,726—IPR2016-01297, Ex.1024 U.S. Pat. No. 3,203,025 ("Schreur"), Jun. 28, 2016.
Nu Mark LLC, Petition for Inter Partes Review of U.S. Pat. No. 8,893,726—IPR2016-01297, Ex.1025 U.S. Appl. No. 2001/0026788 ("Piskorz"), Jun. 28, 2016.
Nu Mark LLC, Petition for Inter Partes Review of U.S. Pat. No. 8,893,726—IPR2016-01297, Ex.1026 European Patent Application No. EP0845220 B1 ("Susa"), Jun. 28, 2016.
Nu Mark LLC, Petition for Inter Partes Review of U.S. Pat. No. 8,893,726—IPR2016-01297, Ex.1027 U.S. Pat. No. 5,745,985 ("Ghosh"), Jun. 28, 2016.
Nu Mark LLC, Petition for Inter Partes Review of U.S. Pat. No. 8,893,726—IPR2016-01297, Ex.1028 U.S. Pat. No. 4,676,237 ("Wood"), Jun. 28, 2016.
Nu Mark LLC, Petition for Inter Partes Review of U.S. Pat. No. 8,893,726—IPR2016-01297, Ex.1029 U.S. Pat. No. 4,945,448 ("Bremenour"), Jun. 28, 2016.
Nu Mark LLC, Petition for Inter Partes Review of U.S. Pat. No. 8,893,726—IPR2016-01297, Ex.1030 Certified Translation of Chinese Utility Model Publication No. CN1233436A ("Hongbin"), Jun. 28, 2016.
Nu Mark LLC, Petition for Inter Partes Review of U.S. Pat. No. 8,893,726—IPR2016-01297, Ex.1031 Decision—Denying Institution of Inter Partes Review, Case No. IPR2015-01302 ("726 Decision"), Jun. 28, 2016.
Nu Mark LLC, Petition for Inter Partes Review of U.S. Pat. No. 8,893,726—IPR2016-01297, Ex.1032 U.S. Pat. No. 6,102,036 ("Slutsky"), Jun. 28, 2016.

(56) References Cited

OTHER PUBLICATIONS

Nu Mark LLC, Petition for Inter Partes Review of U.S. Pat. No. 8,893,726—IPR2016-01297, Ex.1033 Decision—Institution of Inter Partes Review, Case No. IPR2014-00424 ("148 Decision"), Jun. 28, 2016.
Nu Mark LLC, Petition for Inter Partes Review of U.S. Pat. No. 8,893,726—IPR2016-01297, Ex.1034 U.S. Pat. No. 6,491,233 ("Nichols"), Jun. 28, 2016.
USPTO PTAB, *Nu Mark LLC v. Fontem Holdings 1 B.V.*, IPR2016-01299, Paper 11, Decision Instituting Inter Partes Review, Dec. 14, 2017.
Nu Mark LLC, Petition for Inter Partes Review of U.S. Pat. No. 8,393,331—IPR2016-01299, Paper 1, Jun. 28, 2016.
Nu Mark LLC, Petition for Inter Partes Review of U.S. Pat. No. 8,393,331—IPR2016-01299, Ex. 1001 U.S. Pat. No. 8,393,331 ("the 331 Patent"), Jun. 28, 2016.
Nu Mark LLC, Petition for Inter Partes Review of U.S. Pat. No. 8,393,331—IPR2016-01299, Ex. 1002 File History for U.S. Pat. No. 8,393,331, Jun. 28, 2016.
Nu Mark LLC, Petition for Inter Partes Review of U.S. Pat. No. 8,393,331—IPR2016-01299, Ex. 1003 Declaration of John M. Collins, Ph.D. ("Collins Decl."), Jun. 28, 2016.
Nu Mark LLC, Petition for Inter Partes Review of U.S. Pat. No. 8,393,331—IPR2016-01299, Ex. 1004 U.S. Pat. No. 6,155,268 ("Takeuchi"), Jun. 28, 2016.
Nu Mark LLC, Petition for Inter Partes Review of U.S. Pat. No. 8,393,331—IPR2016-01299, Ex. 1005 U.S. Pat. No. 2,057,353 ("Whittemore"), Jun. 28, 2016.
Nu Mark LLC, Petition for Inter Partes Review of U.S. Pat. No. 8,393,331—IPR2016-01299, Ex. 1006 U.S. Pat. No. 4,947,874 ("Brooks 874"), Jun. 28, 2016.
Nu Mark LLC, Petition for Inter Partes Review of U.S. Pat. No. 8,393,331—IPR2016-01299, Ex. 1007 Decision—Institution of Inter Partes Review, Case No. IPR2014-01289 ("331 Decision"), Jun. 28, 2016.
Nu Mark LLC, Petition for Inter Partes Review of U.S. Pat. No. 8,393,331—IPR2016-01299, Ex. 1008 Order to Terminate Proceedings, Case No. IPR2014-01300, Jun. 28, 2016.
Nu Mark LLC, Petition for Inter Partes Review of U.S. Pat. No. 8,393,331—IPR2016-01299, Ex. 1009 U.S. Pat. No. 5,743,251 ("Howell"), Jun. 28, 2016.
Nu Mark LLC, Petition for Inter Partes Review of U.S. Pat. No. 8,393,331—IPR2016-01299, Ex. 1010 U.S. Pat. No. 6,598,607 ("Adiga"), Jun. 28, 2016.
Nu Mark LLC, Petition for Inter Partes Review of U.S. Pat. No. 8,393,331—IPR2016-01299, Ex. 1011 U.S. Pat. No. 5,894,841 ("Voges"), Jun. 28, 2016.
Nu Mark LLC, Petition for Inter Partes Review of U.S. Pat. No. 8,393,331—IPR2016-01299, Ex. 1012 U.S. Pat. No. 4,990,939 ("Sekiya"), Jun. 28, 2016.
Nu Mark LLC, Petition for Inter Partes Review of U.S. Pat. No. 8,393,331—IPR2016-01299, Ex. 1013 U.S. Pat. No. 4,771,295 ("Baker"), Jun. 28, 2016.
Nu Mark LLC, Petition for Inter Partes Review of U.S. Pat. No. 8,393,331—IPR2016-01299, Ex. 1014 U.S. Pat. No. 5,703,633 ("Gehrer"), Jun. 28, 2016.
Nu Mark LLC, Petition for Inter Partes Review of U.S. Pat. No. 8,393,331—IPR2016-01299, Ex. 1015 U.S. Pat. No. 5,497,791 ("Bowen"), Jun. 28, 2016.
Nu Mark LLC, Petition for Inter Partes Review of U.S. Pat. No. 8,393,331—IPR2016-01299, Ex. 1016 U.S. Pat. No. 4,797,692 ("Ims"), Jun. 28, 2016.
Nu Mark LLC, Petition for Inter Partes Review of U.S. Pat. No. 8,393,331—IPR2016-01299, Ex. 1017 Thermal Ink-Jet Print Cartridge Designers Guide ("Ink-Jet Guide"), Jun. 28, 2016.
Nu Mark LLC, Petition for Inter Partes Review of U.S. Pat. No. 8,393,331—IPR2016-01299, Ex. 1018 U.S. Appl. No. 2006/0,093,977 ("Pellizzari I"), Jun. 28, 2016.

Nu Mark LLC, Petition for Inter Partes Review of U.S. Pat. No. 8,393,331—IPR2016-01299, Ex. 1019 U.S. Pat. No. 7,059,307 ("Pellizzari II"), Jun. 28, 2016.
Nu Mark LLC, Petition for Inter Partes Review of U.S. Pat. No. 8,393,331—IPR2016-01299, Ex. 1020 U.S. Pat. No. 3,502,588 ("Winberg"), Jun. 28, 2016.
Nu Mark LLC, Petition for Inter Partes Review of U.S. Pat. No. 8,393,331—IPR2016-01299, Ex. 1021 U.S. Pat. No. 6,234,167 ("Cox"), Jun. 28, 2016.
Nu Mark LLC, Petition for Inter Partes Review of U.S. Pat. No. 8,393,331—IPR2016-01299, Ex. 1022 U.S. Pat. No. 5,666,977 ("Higgins"), Jun. 28, 2016.
Nu Mark LLC, Petition for Inter Partes Review of U.S. Pat. No. 8,393,331—IPR2016-01299, Ex. 1023 European Patent Application No. 0358114 A2 ("Brooks 114"), Jun. 28, 2016.
Nu Mark LLC, Petition for Inter Partes Review of U.S. Pat. No. 8,393,331—IPR2016-01299, Ex. 1024 U.S. Pat. No. 7,284,424 ("Kanke"), Jun. 28, 2016.
Nu Mark LLC, Petition for Inter Partes Review of U.S. Pat. No. 8,393,331—IPR2016-01299, Ex. 1025 U.S. Pat. No. 5,224,265 ("Dux"), Jun. 28, 2016.
Nu Mark LLC, Petition for Inter Partes Review of U.S. Pat. No. 8,393,331—IPR2016-01299, Ex. 1026 U.S. Pat. No. 6,620,659 ("Emmma"), Jun. 28, 2016.
Nu Mark LLC, Petition for Inter Partes Review of U.S. Pat. No. 8,393,331—IPR2016-01299, Ex. 1027 U.S. Pat. No. 5,745,985 ("Ghosh"), Jun. 28, 2016.
Nu Mark LLC, Petition for Inter Partes Review of U.S. Pat. No. 8,393,331—IPR2016-01299, Ex. 1028 U.S. Pat. No. 4,676,237 ("Wood"), Jun. 28, 2016.
Nu Mark LLC, Petition for Inter Partes Review of U.S. Pat. No. 8,393,331—IPR2016-01299, Ex. 1029 U.S. Pat. No. 4,945,448 ("Bremenour"), Jun. 28, 2016.
Nu Mark LLC, Petition for Inter Partes Review of U.S. Pat. No. 8,393,331—IPR2016-01299, Ex. 1030 Certified Translation of Chinese Utility Model Publication No. CN 1233436A ("Hongbin"), Jun. 28, 2016.
Nu Mark LLC, Petition for Inter Partes Review of U.S. Pat. No. 8,393,331—IPR2016-01299, Ex. 1031 U.S. Pat. No. 6,196,218 ("Voges 218"), Jun. 28, 2016.
Nu Mark LLC, Petition for Inter Partes Review of U.S. Pat. No. 8,393,331—IPR2016-01299, Ex. 1032 U.S. Pat. No. 3,747,120 ("Stemme"), Jun. 28, 2016.
Nu Mark LLC, Petition for Inter Partes Review of U.S. Pat. No. 8,393,331—IPR2016-01299, Ex. 1033 Decision—Institution of Inter Partes Review—IPR2014-00424 ("148 Decision"), Jun. 28, 2016.
Nu Mark LLC, Petition for Inter Partes Review of U.S. Pat. No. 8,393,331—IPR2016-01299, Ex. 1034 U.S. Pat. No. 3,200,819 ("Gilbert"), Jun. 28, 2016.
Nu Mark LLC, Petition for Inter Partes Review of U.S. Pat. No. 8,393,331—IPR2016-01299, Ex. 1035 U.S. Pat. No. 6,501,052 ("Cox II"), Jun. 28, 2016.
Nu Mark LLC, Petition for Inter Partes Review of U.S. Pat. No. 8,393,331—IPR2016-01299, Ex. 1036 U.S. Pat. No. 6,491,233 ("Nichols"), Jun. 28, 2016.
USPTO PTAB, *Nu Mark LLC v. Fontem Holdings 1 B.V.*, IPR2016-01438 Paper 13, Decision Denying Inter Partes Review, Dec. 29, 2016.
Nu Mark LLC, Petition for Inter Partes Review of U.S. Pat. No. 8,393,331—IPR2016-01438, Paper 1 Petition Jul. 14, 2016.
Nu Mark LLC, Petition for Inter Partes Review of U.S. Pat. No. 8,393,331—IPR2016-01438, Ex.1101 U.S. Pat. No. 8,393,331 (the "331 Patent"), Jul. 14, 2016.
Nu Mark LLC, Petition for Inter Partes Review of U.S. Pat. No. 8,393,331—IPR2016-01438, Ex.1102 File History for U.S. Pat. No. 8,393,331, Jul. 14, 2016.
Nu Mark LLC, Petition for Inter Partes Review of U.S. Pat. No. 8,393,331—IPR2016-01438, Ex.1103 Declaration of John M. Collins, Ph.D., Jul. 14, 2016.
Nu Mark LLC, Petition for Inter Partes Review of U.S. Pat. No. 8,393,331—IPR2016-01438, Ex.1104 Curriculum Vitae of Dr. John M. Collins, Jul. 14, 2016.

(56) References Cited

OTHER PUBLICATIONS

Nu Mark LLC, Petition for Inter Partes Review of U.S. Pat. No. 8,393,331—IPR2016-01438, Ex.1105 U.S. Appl. No. 2007/0,267,031 A1 ("Hon 031"), Jul. 14, 2016.
Nu Mark LLC, Petition for Inter Partes Review of U.S. Pat. No. 8,393,331—IPR2016-01438, Ex.1106 File History for U.S. Appl. No. 12/944,123, filed Jul. 14, 2016.
Nu Mark LLC, Petition for Inter Partes Review of U.S. Pat. No. 8,393,331—IPR2016-01438, Ex.1107 Substitute Specification filed in U.S. Appl. No. 12/944,123, filed Jul. 14, 2016.
Nu Mark LLC, Petition for Inter Partes Review of U.S. Pat. No. 8,393,331—IPR2016-01438, Ex.1108 File History for U.S. Appl. No. 10/587,707 (now U.S. Pat. No. 7,832,410), Jul. 14, 2016.
Nu Mark LLC, Petition for Inter Partes Review of U.S. Pat. No. 8,393,331—IPR2016-01438, Ex.1109 Certified Translation of CN 20040031182, Jul. 14, 2016.
Nu Mark LLC, Petition for Inter Partes Review of U.S. Pat. No. 8,393,331—IPR2016-01438, Ex.1110 Decision Instituting Inter Partes Review—IPR2014-01289, Jul. 14, 2016.
Nu Mark LLC, Petition for Inter Partes Review of U.S. Pat. No. 8,393,331—IPR2016-01438, Ex.1111 Claim Construction Order, *Fontem Ventures B. V. et al.* v. *Njoy, Inc. et al.*, Civil Action No. 2:14-cv-1645 (C.D. Cal.), Jan. 29, 2015, Jul. 14, 2016.
Nu Mark LLC, Petition for Inter Partes Review of U.S. Pat. No. 8,393,331—IPR2016-01438, Ex.1112 U.S. Pat. No. 7,832,410 (the "410 Patent"), Jul. 14, 2016.
Nu Mark LLC, Petition for Inter Partes Review of U.S. Pat. No. 8,393,331—IPR2016-01438, Ex.1113 U.S. Pat. No. 8,689,805 (the "805 Patent"), Jul. 14, 2016.
Nu Mark LLC, Petition for Inter Partes Review of U.S. Pat. No. 8,393,331—IPR2016-01438, Ex.1114 File History for U.S. Appl. No. 13/426,817 (now U.S. Pat. No. 8,689,805), Jul. 14, 2016.
Nu Mark LLC, Petition for Inter Partes Review of U.S. Pat. No. 8,393,331—IPR2016-01438, Ex.1115 EP1736065 A1, Jul. 14, 2016.
Nu Mark LLC, Petition for Inter Partes Review of U.S. Pat. No. 8,393,331—IPR2016-01438, Ex.1116 Complaint, *Fontem Ventures B. V., et al.* v. *Nu Mark LLC*, Case No. 2:16-cv-02291 (excerpt), Jul. 14, 2016.
Nu Mark LLC, Petition for Inter Partes Review of U.S. Pat. No. 8,393,331—IPR2016-01438, Ex.1117 Certified Translation of WO 2005/099494, Jul. 14, 2016.
Nu Mark LLC, Petition for Inter Partes Review of U.S. Pat. No. 8,393,331—IPR2016-01438, Ex.1118 WO 2005/099494 Chinese version with English abstract (face), Jul. 14, 2016.
USPTO PTAB, *R.J. Reynolds Vapor Co.* v. *Fontem Holdings 1 B.V.*, IPR2016-01527, Paper 10, Decision Denying Inter Partes Review, Jan. 30, 2017.
R.J. Reynolds Vapor Company, Petition for Inter Partes Review of U.S. Pat. No. 8,490,628—IPR2016-01527, Paper 1 Petition, Aug. 3, 2016.
R.J. Reynolds Vapor Company, Petition for Inter Partes Review of U.S. Pat. No. 8,490,628—IPR2016-01527, Ex. 1001 U.S. Pat. No. 8,490,628 ("the '628 patent"), Aug. 3, 2016.
R.J. Reynolds Vapor Company, Petition for Inter Partes Review of U.S. Pat. No. 8,490,628—IPR2016-01527, Ex. 1002 The '628 Patent File History, Aug. 3, 2016.
R.J. Reynolds Vapor Company, Petition for Inter Partes Review of U.S. Pat. No. 8,490,628—IPR2016-01527, Ex. 1003 U.S. Pat. No. 6,155,268 ("Takeuchi"), Aug. 3, 2016.
R.J. Reynolds Vapor Company, Petition for Inter Partes Review of U.S. Pat. No. 8,490,628—IPR2016-01527, Ex. 1004 U.S. Pat. No. 2,057,353 ("Whittemore"), Aug. 3, 2016.
R.J. Reynolds Vapor Company, Petition for Inter Partes Review of U.S. Pat. No. 8,490,628—IPR2016-01527, Ex. 1005 U.S. Pat. No. 5,894,841 ("Voges"), Aug. 3, 2016.
R.J. Reynolds Vapor Company, Petition for Inter Partes Review of U.S. Pat. No. 8,490,628—IPR2016-01527, Ex. 1006 U.S. Pat. No. 5,703,633 ("Gehrer"), Aug. 3, 2016.
R.J. Reynolds Vapor Company, Petition for Inter Partes Review of U.S. Pat. No. 8,490,628—IPR2016-01527, Ex. 1007 "Thermal Ink-Jet Print Cartridge Designers Guide" (2nd Edition Hewlett Packard), Aug. 3, 2016.
R.J. Reynolds Vapor Company, Petition for Inter Partes Review of U.S. Pat. No. 8,490,628—IPR2016-01527, Ex. 1008 IPR2014-01300 Paper 8: Decision for Inter Partes Review Institution, Aug. 3, 2016.
R.J. Reynolds Vapor Company, Petition for Inter Partes Review of U.S. Pat. No. 8,490,628—IPR2016-01527, Ex. 1009 IPR2014-01300 Paper 2: Inter Partes Review Petition, Aug. 3, 2016.
R.J. Reynolds Vapor Company, Petition for Inter Partes Review of U.S. Pat. No. 8,490,628—IPR2016-01527, Ex. 1010 Expert Declaration of Robert Sturges, Ph.D. ("Sturges Decl."), Aug. 3, 2016.
R.J. Reynolds Vapor Company, Petition for Inter Partes Review of U.S. Pat. No. 8,490,628—IPR2016-01527, Ex. 1011 U.S. Pat. No. 5,743,251 ("Howell"), Aug. 3, 2016.
R.J. Reynolds Vapor Company, Petition for Inter Partes Review of U.S. Pat. No. 8,490,628—IPR2016-01527, Ex. 1012 U.S. Pat. No. 1,514,682 ("Wilson"), Aug. 3, 2016.
R.J. Reynolds Vapor Company, Petition for Inter Partes Review of U.S. Pat. No. 8,490,628—IPR2016-01527, Ex. 1013 U.S. Pat. No. 4,947,874 ("Brooks"), Aug. 3, 2016.
R.J. Reynolds Vapor Company, Petition for Inter Partes Review of U.S. Pat. No. 8,490,628—IPR2016-01527, Ex. 1014 U.S. Pat. No. 5,745,985 ("Ghosh"), Aug. 3, 2016.
R.J. Reynolds Vapor Company, Petition for Inter Partes Review of U.S. Pat. No. 8,490,628—IPR2016-01527, Ex. 1015 U.S. Pat. No. 4,676,237 ("Wood"), Aug. 3, 2016.
R.J. Reynolds Vapor Company, Petition for Inter Partes Review of U.S. Pat. No. 8,490,628—IPR2016-01527, Ex. 1016 U.S. Pat. No. 4,945,448 ("Bremenour"), Aug. 3, 2016.
R.J. Reynolds Vapor Company, Petition for Inter Partes Review of U.S. Pat. No. 8,490,628—IPR2016-01527, Ex. 1017 U.S. Pat. No. 6,322,269 ("Kaufman"), Aug. 3, 2016.
R.J. Reynolds Vapor Company, Petition for Inter Partes Review of U.S. Pat. No. 8,490,628—IPR2016-01527, Ex. 1018 U.S. Pat. No. 6,722,763 ("Hsu"), Aug. 3, 2016.
R.J. Reynolds Vapor Company, Petition for Inter Partes Review of U.S. Pat. No. 8,490,628—IPR2016-01527, Ex. 1019 U.S. Pat. No. 5,646,666 ("Cowger"), Aug. 3, 2016.
R.J. Reynolds Vapor Company, Petition for Inter Partes Review of U.S. Pat. No. 8,490,628—IPR2016-01527, Ex. 1020 U.S. Pat. No. 7,284,424 ("Kanke"), Aug. 3, 2016.
R.J. Reynolds Vapor Company, Petition for Inter Partes Review of U.S. Pat. No. 8,490,628—IPR2016-01527, Ex. 1021 U.S. Pat. No. 5,224,265 ("Dux"), Aug. 3, 2016.
R.J. Reynolds Vapor Company, Petition for Inter Partes Review of U.S. Pat. No. 8,490,628—IPR2016-01527, Ex. 1022 U.S. Pat. No. 6,620,659 ("Emmma"), Aug. 3, 2016.
Nu Mark LLC, Petition for Inter Partes Review of U.S. Pat. No. 9,326,549—IPR2016-01664, Aug. 22, 2016.
Nu Mark LLC, Petition for Inter Partes Review of U.S. Pat. No. 9,326,549—IPR2016-01664, Ex.1001 U.S. Pat. No. 9,326,549 (the "549 Patent"), Aug. 22, 2016.
Nu Mark LLC, Petition for Inter Partes Review of U.S. Pat. No. 9,326,549—IPR2016-01664, Ex.1002 File History for U.S. Pat. No. 9,326,549, Aug. 22, 2016.
Nu Mark LLC, Petition for Inter Partes Review of U.S. Pat. No. 9,326,549—IPR2016-01664, Ex.1003 Declaration of John M. Collins, Ph.D., Aug. 22, 2016.
Nu Mark LLC, Petition for Inter Partes Review of U.S. Pat. No. 9,326,549—IPR2016-01664, Ex.1004 Curriculum Vitae of Dr. John M. Collins, Aug. 22, 2016.
Nu Mark LLC, Petition for Inter Partes Review of U.S. Pat. No. 9,326,549—IPR2016-01664, Ex.1005 U.S. Appl. No. 2007/0267031 A1 ("Hon 031"), Aug. 22, 2016.
Nu Mark LLC, Petition for Inter Partes Review of U.S. Pat. No. 9,326,549—IPR2016-01664, Ex.1006 File History for U.S. Appl. No. 12/944,123 (now U.S. Pat. No. 8,393,331), Aug. 22, 2016.

(56) References Cited

OTHER PUBLICATIONS

Nu Mark LLC, Petition for Inter Partes Review of U.S. Pat. No. 9,326,549—IPR2016-01664, Ex.1007 Substitute Specification filed in U.S. Appl. No. 12/944,123 (now U.S. Pat. No. 8,393,331), Aug. 22, 2016.
Nu Mark LLC, Petition for Inter Partes Review of U.S. Pat. No. 9,326,549—IPR2016-01664, Ex.1008 File History for U.S. Appl. No. 10/587,707 (now U.S. Pat. No. 7,832,410), Aug. 22, 2016.
Nu Mark LLC, Petition for Inter Partes Review of U.S. Pat. No. 9,326,549—IPR2016-01664, Ex.1009 Certified Translation of CN 20040031182, Aug. 22, 2016.
Nu Mark LLC, Petition for Inter Partes Review of U.S. Pat. No. 9,326,549—IPR2016-01664, Ex.1010 Decision Instituting Inter Partes Review—IPR2014-01289, Aug. 22, 2016.
Nu Mark LLC, Petition for Inter Partes Review of U.S. Pat. No. 9,326,549—IPR2016-01664, Ex.1011 Claim Construction Order, *Fontem Ventures B.V., et al.* v. *Njoy, Inc., et al.*, Case No. 2:14-cv-01645, Jan. 29, 2015 (Dkt. 65), Aug. 22, 2016.
Nu Mark LLC, Petition for Inter Partes Review of U.S. Pat. No. 9,326,549—IPR2016-01664, Ex.1012 U.S. Pat. No. 7,832,410 (the "410 Patent"), Aug. 22, 2016.
Nu Mark LLC, Petition for Inter Partes Review of U.S. Pat. No. 9,326,549—IPR2016-01664, Ex.1013 U.S. Pat. No. 8,689,805 (the "805 Patent"), Aug. 22, 2016.
Nu Mark LLC, Petition for Inter Partes Review of U.S. Pat. No. 9,326,549—IPR2016-01664, Ex.1014 File History for U.S. Appl. No. 13/426,817 (now U.S. Pat. No. 8,689,805), Aug. 22, 2016.
Nu Mark LLC, Petition for Inter Partes Review of U.S. Pat. No. 9,326,549—IPR2016-01664, Ex.1015 European Patent No. 1736065 A1 to Hon, Aug. 22, 2016.
Nu Mark LLC, Petition for Inter Partes Review of U.S. Pat. No. 9,326,549—IPR2016-01664, Ex.1016 Complaint, *Fontem Ventures B.V., et al.* v. *Nu Mark LLC*, Case No. 2:16-cv-04537, Jun. 22, 2016 (Dkt. 1), Aug. 22, 2016.
Nu Mark LLC, Petition for Inter Partes Review of U.S. Pat. No. 9,326,549—IPR2016-01664, Ex.1017 Certified Translation of WO 2005/099494, Aug. 22, 2016.
USPTO PTAB, *R.J. Reynolds Vapor Co.* v. *Fontem Holdings 1 B.V.*, IPR2016-01859, Paper 8, Decision Denying Inter Partes Review, Mar. 13, 2017.
R.J. Reynolds Vapor Company, Petition for Inter Partes Review of U.S. Pat. No. 9,326,549—IPR2016-01859, Sep. 23, 2016.
R.J. Reynolds Vapor Company, Petition for Inter Partes Review of U.S. Pat. No. 9,326,549—IPR2016-01859, Ex. 1001 U.S. Pat. No. 9,326,549, Sep. 23, 2016.
R.J. Reynolds Vapor Company, Petition for Inter Partes Review of U.S. Pat. No. 9,326,549—IPR2016-01859,Ex. 1002 '549 Patent File History, Sep. 23, 2016.
R.J. Reynolds Vapor Company, Petition for Inter Partes Review of U.S. Pat. No. 9,326,549—IPR2016-01859,Ex. 1003 U.S. Pat. Pub. No. 2007/0267031 A1 to Lik Hon (now U.S. Pat. No. 7,832,410), Sep. 23, 2016.
R.J. Reynolds Vapor Company, Petition for Inter Partes Review of U.S. Pat. No. 9,326,549—IPR2016-01859,Ex. 1004 U.S. Pat. No. 7,832,410, Sep. 23, 2016.
R.J. Reynolds Vapor Company, Petition for Inter Partes Review of U.S. Pat. No. 9,326,549—IPR2016-01859,Ex. 1005 File History for U.S. Pat. No. 7,832,410, Sep. 23, 2016.
R.J. Reynolds Vapor Company, Petition for Inter Partes Review of U.S. Pat. No. 9,326,549—IPR2016-01859,Ex. 1006 Excerpt of File History for U.S. Pat. No. 8,393,331, Sep. 23, 2016.
R.J. Reynolds Vapor Company, Petition for Inter Partes Review of U.S. Pat. No. 9,326,549—IPR2016-01859,Ex. 1007 Substitute Specification filed in U.S. Pat. No. 8,393,331, Sep. 23, 2016.
R.J. Reynolds Vapor Company, Petition for Inter Partes Review of U.S. Pat. No. 9,326,549—IPR2016-01859,Ex. 1008 WO 2005/099494 with English abstract (front page), Sep. 23, 2016.
R.J. Reynolds Vapor Company, Petition for Inter Partes Review of U.S. Pat. No. 9,326,549—IPR2016-01859,Ex. 1009 Certified Translation of WO 2005/099494, Sep. 23, 2016.
R.J. Reynolds Vapor Company, Petition for Inter Partes Review of U.S. Pat. No. 9,326,549—IPR2016-01859,Ex. 1010 Certified Translation of CN 20040031182, Sep. 23, 2016.
R.J. Reynolds Vapor Company, Petition for Inter Partes Review of U.S. Pat. No. 9,326,549—IPR2016-01859,Ex. 1011 U.S. Pat. No. 8,689,805, Sep. 23, 2016.
R.J. Reynolds Vapor Company, Petition for Inter Partes Review of U.S. Pat. No. 9,326,549—IPR2016-01859,Ex. 1012 Excerpt of File History for U.S. Pat. No. 8,689,805, Sep. 23, 2016.
R.J. Reynolds Vapor Company, Petition for Inter Partes Review of U.S. Pat. No. 9,326,549—IPR2016-01859,Ex. 1013 *Njoy, Inc.* v. *Fontem Holdings 1 B.V.*, IPR2014-01289 (PTAB, filed Aug. 14, 2014), Paper No. 8, Sep. 23, 2016.
R.J. Reynolds Vapor Company, Petition for Inter Partes Review of U.S. Pat. No. 9,326,549—IPR2016-01859,Ex. 1014 *Njoy, Inc.* v. *Fontem Holdings 1 B.V.*, IPR2014-01300 (PTAB, filed Aug. 15, 2014), Paper No. 8, Sep. 23, 2016.
R.J. Reynolds Vapor Company, Petition for Inter Partes Review of U.S. Pat. No. 9,326,549—IPR2016-01859,Ex. 1015 *Njoy, Inc.* v. *Fontem Holdings 1 B.V.*, IPR2015-01302 (PTAB, filed May 29, 2015), Paper No. 15, Sep. 23, 2016.
R.J. Reynolds Vapor Company, Petition for Inter Partes Review of U.S. Pat. No. 9,326,549—IPR2016-01859,Ex. 1016 Complaint, *Fontem Ventures B.V. et al.* v. *R.J. Reynolds Vapor Company*, No. 2:16-cv-03049 (C.D. Cal., filed May 3, 2016) (excerpts), Sep. 23, 2016.
R.J. Reynolds Vapor Company, Petition for Inter Partes Review of U.S. Pat. No. 9,326,549—IPR2016-01859,Ex. 1017 Declaration of Robert Sturges, Ph.D., Sep. 23, 2016.
R.J. Reynolds Vapor Company, Petition for Inter Partes Review of U.S. Pat. No. 9,326,549—IPR2016-01859,Ex. 1018 EP 1736065 A1, Sep. 23, 2016.
R.J. Reynolds Vapor Company, Petition for Inter Partes Review of U.S. Pat. No. 9,326,549—IPR2016-01859,Ex. 1019 Claim Construction Order, *Fontem Ventures B.V., et al.* v. *Njoy, Inc., et al.*, Case No. 2:14-cv-01645, Jan. 29, 2015 (Dkt. 65), Sep. 23, 2016.
R.J. Reynolds Vapor Company, Petition for Inter Partes Review of U.S. Pat. No. 8,893,726—IPR2017-01117, Paper 2—Petition, Apr. 4, 2017.
R.J. Reynolds Vapor Company, IPR2017-01117, Ex. 1001—U.S. Pat. No. 8,893,726, Apr. 4, 2017.
R.J. Reynolds Vapor Company, IPR2017-01117, Ex. 1002-726 Patent File History, Non-Final Rejection (Aug. 16, 2013), Apr. 4, 2017.
R.J. Reynolds Vapor Company, IPR2017-01117, Ex. 1003-726 Patent File History, Amendment (Oct. 8, 2013), Apr. 4, 2017.
R.J. Reynolds Vapor Company, IPR2017-01117, Ex. 1004-726 Patent File History, Notice of Allowance (Aug. 18, 2014), Apr. 4, 2017.
R.J. Reynolds Vapor Company, IPR2017-01117, Ex. 1005—*Njoy, Inc.* v. *Fontem Holdings 1 B.V.*, IPR2015-01302 (PTAB, filed May 29, 2015), Paper No. 15, Apr. 4, 2017.
R.J. Reynolds Vapor Company, IPR2017-01117, Ex. 1006—*R.J. Reynolds Vapor Company* v. *Fontem Holdings 1 B.V.*, IPR2016-01270 (PTAB, filed Jul. 2, 2016), Paper No. 11, Apr. 4, 2017.
R.J. Reynolds Vapor Company, IPR2017-01117, Ex. 1007—U.S. Pat. No. 5,144,962, Apr. 4, 2017.
R.J. Reynolds Vapor Company, IPR2017-01117, Ex. 1008—U.S. Pat. No. 4,981,522, Apr. 4, 2017.
R.J. Reynolds Vapor Company, IPR2017-01117, Ex. 1009—Declaration of Robert Sturges, Ph.D., Apr. 4, 2017.
R.J. Reynolds Vapor Company, IPR2017-01117, Ex. 1010—*Njoy, Inc.* v. *Fontem Holdings 1 B.V.*, IPR2015-01302 (PTAB, filed May 29, 2015), Paper No. 6, Apr. 4, 2017.
R.J. Reynolds Vapor Company, IPR2017-01117, Ex. 1011—U.S. Pat. No. 5,894,841, Apr. 4, 2017.
R.J. Reynolds Vapor Company, IPR2017-01117, Ex. 1012—U.S. Pat. No. 6,155,268, Apr. 4, 2017.
R.J. Reynolds Vapor Company, IPR2017-01117, Ex. 1013—U.S. Pat. No. 5,129,409, Apr. 4, 2017.
R.J. Reynolds Vapor Company, IPR2017-01117, Ex. 1014—U.S. Pat. No. 1,016,844, Apr. 4, 2017.

(56) References Cited

OTHER PUBLICATIONS

R.J. Reynolds Vapor Company, IPR2017-01117, Ex. 1015—U.S. Pat. No. 3,385,303, Apr. 4, 2017.
R.J. Reynolds Vapor Company, IPR2017-01117, Ex. 1016—U.S. Pat. No. 3,428,053, Apr. 4, 2017.
R.J. Reynolds Vapor Company, IPR2017-01117, Ex. 1017—U.S. Pat. No. 3,860,012, Apr. 4, 2017.
R.J. Reynolds Vapor Company, IPR2017-01117, Ex. 1018—U.S. Pat. No. 4,270,552, Apr. 4, 2017.
R.J. Reynolds Vapor Company, IPR2017-01117, Ex. 1019—U.S. Pat. No. 4,589,428, Apr. 4, 2017.
R.J. Reynolds Vapor Company, IPR2017-01117, Ex. 1020—U.S. Pat. No. 5,745,985, Apr. 4, 2017.
R.J. Reynolds Vapor Company, IPR2017-01117, Ex. 1021—U.S. Pat. No. 4,208,005, Apr. 4, 2017.
R.J. Reynolds Vapor Company, IPR2017-01117, Ex. 1022—Excerpt from James W. Dally, Packaging of Electronic Systems: A Mechanical Engineering Approach (1990), Apr. 4, 2017.
R.J. Reynolds Vapor Company, Petition for Inter Partes Review of U.S. Pat. No. 8,490,628—1PR2017-01118, Paper 2, Apr. 3, 2017.
R.J. Reynolds Vapor Company, IPR2017-01118 Exhibit-1001—U.S. Pat. No. 8,490,628, Apr. 3, 2017.
R.J. Reynolds Vapor Company, IPR2017-01118 Exhibit-1002—Expert Declaration of Robert Sturges, Ph.D., Apr. 3, 2017.
R.J. Reynolds Vapor Company, IPR2017-01118 Exhibit-1003—U.S. Pat. No. 6,155,268, Apr. 3, 2017.
R.J. Reynolds Vapor Company, IPR2017-01118 Exhibit-1004—U.S. Pat. No. 2,057,353, Apr. 3, 2017.
R.J. Reynolds Vapor Company, IPR2017-01118 Exhibit-1005—The '628 Patent File History, Apr. 3, 2017.
R.J. Reynolds Vapor Company, IPR2017-01118 Exhibit-1006—IPR2016-01527 Paper 10: Decision for Inter Partes Review Institution, Apr. 3, 2017.
R.J. Reynolds Vapor Company, IPR2017-01118 Exhibit-1007—IPR2016-01283 Paper 12: Decision for Inter Partes Review Institution, Apr. 3, 2017.
R.J. Reynolds Vapor Company, IPR2017-01118 Exhibit-1008—IPR2016-01285 Paper 10: Decision for Inter Partes Review Institution, Apr. 3, 2017.
R.J. Reynolds Vapor Company, IPR2017-01118 Exhibit-1009—IPR2014-01300 Paper 8: Decision for Inter Partes Review Institution, Apr. 3, 2017.
R.J. Reynolds Vapor Company, IPR2017-01118 Exhibit-1010—U.S. Pat. No. 5,743,251, Apr. 3, 2017.
R.J. Reynolds Vapor Company, IPR2017-01118 Exhibit-1011—U.S. Pat. No. 1,514,682, Apr. 3, 2017.
R.J. Reynolds Vapor Company, IPR2017-01118 Exhibit-1012—U.S. Pat. No. 7,284,424, Apr. 3, 2017.
R.J. Reynolds Vapor Company, IPR2017-01118 Exhibit-1013—U.S. Pat. No. 4,947,874, Apr. 3, 2017.
R.J. Reynolds Vapor Company, IPR2017-01118 Exhibit-1014—U.S. Pat. No. 5,745,985, Apr. 3, 2017.
R.J. Reynolds Vapor Company, IPR2017-01118 Exhibit-1015—U.S. Pat. No. 4,208,005, Apr. 3, 2017.
R.J. Reynolds Vapor Company, IPR2017-01118 Exhibit-1016—U.S. Pat. No. 4,945,448, Apr. 3, 2017.
R.J. Reynolds Vapor Company, IPR2017-01118 Exhibit-1017—U.S. Pat. No. 5,144,962, Apr. 3, 2017.
R.J. Reynolds Vapor Company, IPR2017-01118 Exhibit-1018—9th Ed., Mark's Standard Handbook for Mechanical Engineers, Eugene A. Avallone et al., published 1978, p. 15-6, Apr. 3, 2017.
R.J. Reynolds Vapor Company, IPR2017-01118 Exhibit-1019—Excerpts from James W. Daily, Packaging of Electronic Systems: A Mechanical Engineering Approach (1990), Apr. 3, 2017.
R.J. Reynolds Vapor Company, IPR2017-01118 Exhibit-1020—U.S. Pat. No. 6,598,607, Apr. 3, 2017.
R.J. Reynolds Vapor Company, IPR2017-01118 Exhibit-1021—U.S. Pat. No. 4,793,365, Apr. 3, 2017.
R.J. Reynolds Vapor Company, IPR2017-01118 Exhibit-1022—U.S. Pat. No. 5,203,355, Apr. 3, 2017.
R.J. Reynolds Vapor Company, IPR2017-01118 Exhibit-1023—U.S. Pat. No. 2,472,282, Apr. 3, 2017.
R.J. Reynolds Vapor Company, IPR2017-01118 Exhibit-1024—U.S. Pat. No. 2,032,695, Apr. 3, 2017.
R.J. Reynolds Vapor Company, IPR2017-01118 Exhibit-1025—Wire, Merriam-Webster's Collegiate Dictionary (10th ed. 2002), Apr. 3, 2017.
R.J. Reynolds Vapor Company, IPR2017-01118 Exhibit-1026—Declaration of James Donnelly, Apr. 3, 2017.
R.J. Reynolds Vapor Company, Petition for Inter Partes Review of U.S. Pat. No. 8,490,628—IPR2017-01119, Paper 2, Apr. 4, 2017.
R.J. Reynolds Vapor Company, IPR2017-01119, Ex. 1001—U.S. Pat. No. 8,490,628, Apr. 4, 2017.
R.J. Reynolds Vapor Company, IPR2017-01119, Ex. 1002—Certified translation of CN 20040031182, Apr. 4, 2017.
R.J. Reynolds Vapor Company, IPR2017-01119, Ex. 1003—U.S. Pat. Pub. No. 2007/0267031 A1 to Lik Hon (now U.S. Pat. No. 7,832,410), Apr. 4, 2017.
R.J. Reynolds Vapor Company, IPR2017-01119, Ex. 1004—U.S. Pat. No. 7,832,410, Apr. 4, 2017.
R.J. Reynolds Vapor Company, IPR2017-01119, Ex. 1005—File History for App. No. 10/587,707 (now U.S. Pat. No. 7,832,410), Apr. 4, 2017.
R.J. Reynolds Vapor Company, IPR2017-01119, Ex. 1006—Excerpt of File History for App. No. 12/944,123 (now U.S. Pat. No. 8,393,331), Apr. 4, 2017.
R.J. Reynolds Vapor Company, IPR2017-01119, Ex. 1007—Substitute Specification filed in App. No. 12/944,123 (now U.S. Pat. No. 8,393,331), Apr. 4, 2017.
R.J. Reynolds Vapor Company, IPR2017-01119, Ex. 1008—Declaration of Robert Sturges, Ph.D., Apr. 4, 2017.
R.J. Reynolds Vapor Company, IPR2017-01119, Ex. 1009—U.S. Pat. No. 8,393,331, Apr. 4, 2017.
R.J. Reynolds Vapor Company, IPR2017-01119, Ex. 1010-IPR2016-01283 Paper 12: Institution Decision for Inter Partes Review, Apr. 4, 2017.
R.J. Reynolds Vapor Company, IPR2017-01119, Ex. 1011—U.S. Pat. No. 8,689,805, Apr. 4, 2017.
R.J. Reynolds Vapor Company, IPR2017-01119, Ex. 1012—File History for App. No. 13/426,817 (now 8,689,805), Apr. 4, 2017.
R.J. Reynolds Vapor Company, IPR2017-01119, Ex. 1013-IPR2016-01859 Paper 8: Institution Decision for Inter Partes Review, Apr. 4, 2017.
R.J. Reynolds Vapor Company, IPR2017-01119, Ex. 1014-IPR2014-01300 Paper 8: Institution Decision for Inter Partes Review, Apr. 4, 2017.
R.J. Reynolds Vapor Company, IPR2017-01119, Ex. 1015—Certified Translation of WO 2005/099494, Apr. 4, 2017.
R.J. Reynolds Vapor Company, Petition for Inter Partes Review of U.S. Pat. No. 8,893,726—1PR2017-01180, Paper 2—Apr. 4, 2017.
R.J. Reynolds Vapor Company, IPR2017-01180, Ex. 1001—U.S. Pat. No. 8,893,726, Apr. 4, 2017.
R.J. Reynolds Vapor Company, IPR2017-01180, Ex. 1002—Certified translation of CN 20040031182, Apr. 4, 2017.
R.J. Reynolds Vapor Company, IPR2017-01180, Ex. 1003—U.S. Pat. Pub. No. 2007/0267031 A1 to Lik Hon (issued as U.S. Pat. No. 7,832,410), Apr. 4, 2017.
R.J. Reynolds Vapor Company, IPR2017-01180, Ex. 1004—U.S. Pat. No. 7,832,410, Apr. 4, 2017.
R.J. Reynolds Vapor Company, IPR2017-01180, Ex. 1005—File History for App. No. 10/587,707 (now U.S. Pat. No. 7,832,410), Apr. 4, 2017.
R.J. Reynolds Vapor Company, IPR2017-01180, Ex. 1006—Excerpt of File History for App. No. 12/944,123 (now U.S. Pat. No. 8,393,331), Apr. 4, 2017.
R.J. Reynolds Vapor Company, IPR2017-01180, Ex. 1007—Substitute Specification filed in U.S. Appl. No. 12/944,123 (now U.S. Pat. No. 8,393,331), Apr. 4, 2017.
R.J. Reynolds Vapor Company, IPR2017-01180, Ex. 1008—Declaration of Robert Sturges, Ph.D., Apr. 4, 2017.
R.J. Reynolds Vapor Company, IPR2017-01180, Ex. 1009—U.S. Pat. No. 8,393,331, Apr. 4, 2017.

(56) References Cited

OTHER PUBLICATIONS

R.J. Reynolds Vapor Company, IPR2017-01180, Ex. 1010-IPR2016-01288 Paper 20: Termination Dismissing the Petitions, Apr. 4, 2017.
R.J. Reynolds Vapor Company, IPR2017-01180, Ex. 1011—U.S. Pat. No. 8,689,805, Apr. 4, 2017.
R.J. Reynolds Vapor Company, IPR2017-01180, Ex. 1012—File History for U.S. Appl. No. 13/426,817 (now 8,689,805), Apr. 4, 2017.
R.J. Reynolds Vapor Company, IPR2017-01180, Ex. 1013—IPR2016-01859 Paper 8: Institution Decision for Inter Partes Review, Apr. 4, 2017.
R.J. Reynolds Vapor Company, IPR2017-01180, Ex. 1015—Certified Translation of WO 2005/099494, Apr. 4, 2017.
R.J. Reynolds Vapor Company, Petition for Inter Partes Review of U.S. Pat. No. 9,326,549—IPR2017-01318, Paper 2—Petition, May 1, 2017.
R.J. Reynolds Vapor Company, Petition for Inter Partes Review of U.S. Pat. No. 9,326,549—IPR2017-01318, Exhibit 1001—U.S. Pat. No. 9,326,549, May 1, 2017.
R.J. Reynolds Vapor Company, Petition for Inter Partes Review of U.S. Pat. No. 9,326,549—IPR2017-01318, Exhibit 1002—Certified translation of CN20040031182, May 1, 2017.
R.J. Reynolds Vapor Company, Petition for Inter Partes Review of U.S. Pat. No. 9,326,549—IPR2017-01318, Exhibit 1003—U.S. Pat. Pub. No. 2007/0267031 to Lik Hon, (now U.S. Pat. No. 7,832,410), May 1, 2017.
R.J. Reynolds Vapor Company, Petition for Inter Partes Review of U.S. Pat. No. 9,326,549—IPR2017-01318, Exhibit 1004—U.S. Pat. No. 7,832,410, May 1, 2017.
R.J. Reynolds Vapor Company, Petition for Inter Partes Review of U.S. Pat. No. 9,326,549—IPR2017-01318, Exhibit 1005—File History for U.S. 10/587,707 (now U.S. Pat. No. 7,832,410), May 1, 2017.
R.J. Reynolds Vapor Company, Petition for Inter Partes Review of U.S. Pat. No. 9,326,549—IPR2017-01318, Exhibit 1006—Excerpt of File History for U.S. 12/944,123 (now U.S. Pat. No. 8,393,331), May 1, 2017.
R.J. Reynolds Vapor Company, Petition for Inter Partes Review of U.S. Pat. No. 9,326,549—IPR2017-01318, Exhibit 1007—Substitute Specification filed in U.S. Appl. No. 12/944,123 (issued as U.S. Pat. No. 8,393,331), May 1, 2017.
R.J. Reynolds Vapor Company, Petition for Inter Partes Review of U.S. Pat. No. 9,326,549—IPR2017-01318, Exhibit 1008—Declaration of Dr. Robert H. Sturges, May 1, 2017.
R.J. Reynolds Vapor Company, Petition for Inter Partes Review of U.S. Pat. No. 9,326,549—IPR2017-01318, Exhibit 1009—U.S. Pat. No. 8,393,331, May 1, 2017.
R.J. Reynolds Vapor Company, Petition for Inter Partes Review of U.S. Pat. No. 9,326,549—IPR2017-01318, Exhibit 1011—U.S. Pat. No. 8,689,805, May 1, 2017.
R.J. Reynolds Vapor Company, Petition for Inter Partes Review of U.S. Pat. No. 9,326,549—IPR2017-01318, Exhibit 1012—Excerpt of File History for 805 patent, May 1, 2017.
R.J. Reynolds Vapor Company, Petition for Inter Partes Review of U.S. Pat. No. 9,326,549—IPR2017-01318, Exhibit 1013—IPR2016-01859, Paper 8, Decision Denying Institution, May 1, 2017.
R.J. Reynolds Vapor Company, Petition for Inter Partes Review of U.S. Pat. No. 9,326,549—IPR2017-01318, Exhibit 1015—Certified translation of WO2005099494, May 1, 2017.
R.J. Reynolds Vapor Company, Petition for Inter Partes Review of U.S. Pat. No. 9,326,549—IPR2017-01319, Paper 2—Petition, May 3, 2017.
R.J. Reynolds Vapor Company, Petition for Inter Partes Review of U.S. Pat. No. 9,326,549—IPR2017-01319, Exhibit 1001—U.S. Pat. No. 9,326,549, May 3, 2017.
R.J. Reynolds Vapor Company, Petition for Inter Partes Review of U.S. Pat. No. 9,326,549—IPR2017-01319, Exhibit 1002—Declaration of Dr. Robert H. Sturges, May 3, 2017.
R.J. Reynolds Vapor Company, Petition for Inter Partes Review of U.S. Pat. No. 9,326,549—IPR2017-01319, Exhibit 1003—CN1233436A, May 3, 2017.
R.J. Reynolds Vapor Company, Petition for Inter Partes Review of U.S. Pat. No. 9,326,549—IPR2017-01319, Exhibit 1004—Certified Translation of CN1233436A to Hongbin, May 3, 2017.
R.J. Reynolds Vapor Company, Petition for Inter Partes Review of U.S. Pat. No. 9,326,549—IPR2017-01319, Exhibit 1005—U.S. Pat. No. 2,057,353, May 3, 2017.
R.J. Reynolds Vapor Company, Petition for Inter Partes Review of U.S. Pat. No. 9,326,549—IPR2017-01319, Exhibit 1006—U.S. Pat. No. 4,947,874, May 3, 2017.
R.J. Reynolds Vapor Company, Petition for Inter Partes Review of U.S. Pat. No. 9,326,549—IPR2017-01319, Exhibit 1007—IPR2014-01300, Paper 8, Institution Decision, May 3, 2017.
R.J. Reynolds Vapor Company, Petition for Inter Partes Review of U.S. Pat. No. 9,326,549—IPR2017-01319, Exhibit 1008—16-cv-1255, *Fontem Ventures B.V.* v. *R.J. Reynolds Vapor Co.*, Plaintiffs' Preliminary Claim Constructions and Preliminary Identification of Intrinsic and Extrinsic Evidence, May 3, 2017.
R.J. Reynolds Vapor Company, Petition for Inter Partes Review of U.S. Pat. No. 9,326,549—IPR2017-01319, Exhibit 1009—U.S. Pat. No. 6,598,607, May 3, 2017.
R.J. Reynolds Vapor Company, Petition for Inter Partes Review of U.S. Pat. No. 9,326,549—IPR2017-01319, Exhibit 1010—U.S. Pat. No. 4,793,365, May 3, 2017.
R.J. Reynolds Vapor Company, Petition for Inter Partes Review of U.S. Pat. No. 9,326,549—IPR2017-01319, Exhibit 1011—U.S. Pat. No. 5,203,355, May 3, 2017.
R.J. Reynolds Vapor Company, Petition for Inter Partes Review of U.S. Pat. No. 9,326,549—IPR2017-01319, Exhibit 1012—U.S. Pat. No. 2,472,282, May 3, 2017.
R.J. Reynolds Vapor Company, Petition for Inter Partes Review of U.S. Pat. No. 9,326,549—IPR2017-01319, Exhibit 1013—U.S. Pat. No. 2,032,695, May 3, 2017.
R.J. Reynolds Vapor Company, Petition for Inter Partes Review of U.S. Pat. No. 9,326,549—IPR2017-01319, Exhibit 1014—Certified Translation of CN2293957Y, May 3, 2017.
R.J. Reynolds Vapor Company, Petition for Inter Partes Review of U.S. Pat. No. 9,326,549—IPR2017-01319, Exhibit 1015—U.S. Pat. No. 5,743,251, May 3, 2017.
R.J. Reynolds Vapor Company, Petition for Inter Partes Review of U.S. Pat. No. 9,326,549—IPR2017-01319, Exhibit 1016—U.S. Pat. No. 1,514,682, May 3, 2017.
R.J. Reynolds Vapor Company, Petition for Inter Partes Review of U.S. Pat. No. 9,326,549—IPR2017-01319, Exhibit 1017—U.S. Pat. No. 5,745,985, May 3, 2017.
R.J. Reynolds Vapor Company, Petition for Inter Partes Review of U.S. Pat. No. 9,326,549—IPR2017-01319, Exhibit 1018—U.S. Pat. No. 4,208,005, May 3, 2017.
R.J. Reynolds Vapor Company, Petition for Inter Partes Review of U.S. Pat. No. 9,326,549—IPR2017-01319, Exhibit 1019—U.S. Pat. No. 4,945,448, May 3, 2017.
R.J. Reynolds Vapor Company, Petition for Inter Partes Review of U.S. Pat. No. 9,326,549—IPR2017-01319, Exhibit 1020—Excerpts from James W. Daily, Packaging of Electronic Systems: A Mechanical Engineering Approach (1990), May 3, 2017.
R.J. Reynolds Vapor Company, Petition for Inter Partes Review of U.S. Pat. No. 9,326,549—1PR2017-01319, Exhibit 1021—EP0845220B1, May 3, 2017.
R.J. Reynolds Vapor Company, Petition for Inter Partes Review of U.S. Pat. No. 9,326,549—IPR2017-01319, Exhibit 1022—U.S. Pat. No. 6,155,268, May 3, 2017.
R.J. Reynolds Vapor Company, Petition for Inter Partes Review of U.S. Pat. No. 9,326,549—IPR2017-01319, Exhibit 1023—U.S. Pat. No. 6,501,052, May 3, 2017.
R.J. Reynolds Vapor Company, Petition for Inter Partes Review of U.S. Pat. No. 9,326,549—IPR2017-01319, Exhibit 1024—U.S. Pat. No. 4,981,522, May 3, 2017.
R.J. Reynolds Vapor Company, Petition for Inter Partes Review of U.S. Pat. No. 9,326,549—IPR2017-01319, Exhibit 1025—Excerpts from File History for U.S. 14/719,061 (issued as U.S. Pat. No. 9,326,549), May 3, 2017.

(56) References Cited

OTHER PUBLICATIONS

R.J. Reynolds Vapor Company, Petition for Inter Partes Review of U.S. Pat. No. 9,326,549—IPR2017-01319, Exhibit 1026 —Eugene A. Avallone, Mark's Standard Handbook for Mechanical Engineers, 15-16 (1978), May 3, 2017.
R.J. Reynolds Vapor Company, Petition for Inter Partes Review of U.S. Pat. No. 8,393,331—IPR2018-00627, Paper 2—Petition, Mar. 1, 2018.
R.J. Reynolds Vapor Company, IPR2018-00627, Ex. 1001—U.S. Pat. No. 8,393,331 ("331 patent"), Mar. 1, 2018.
R.J. Reynolds Vapor Company, IPR2018-00627, Ex. 1002—Expert Declaration of Robert Sturges, Ph.D., Mar. 1, 2018.
R.J. Reynolds Vapor Company, IPR2018-00627, Ex. 1003—U.S. Pat. No. 6,155,268 ("Takeuchi"), Mar. 1, 2018.
R.J. Reynolds Vapor Company, IPR2018-00627, Ex. 1004—U.S. Pat. No. 5,743,251 ("Howell"), Mar. 1, 2018.
R.J. Reynolds Vapor Company, IPR2018-00627, Ex. 1005—U.S. Pat. No. 6,598,607 ("Adiga"), Mar. 1, 2018.
R.J. Reynolds Vapor Company, IPR2018-00627, Ex. 1006—U.S. Pat. No. 5,894,841 ("Voges"), Mar. 1, 2018.
R.J. Reynolds Vapor Company, IPR2018-00627, Ex. 1007—U.S. Pat. No. 4,990,939 ("Sekiya"), Mar. 1, 2018.
R.J. Reynolds Vapor Company, IPR2018-00627, Ex. 1008—U.S. Pat. No. 4,771,295 ("Baker"), Mar. 1, 2018.
R.J. Reynolds Vapor Company, IPR2018-00627, Ex. 1009—Institution Decision dated Feb. 19, 2015 (Paper 8), *Njoy, Inc.* v. *Fontem Holdings 1 B.V.*, IPR2014-01289 (P.T.A.B., petition filed Aug. 14, 2014), Mar. 1, 2018.
R.J. Reynolds Vapor Company, IPR2018-00627, Ex. 1010—Termination Order dated Nov. 24, 2015 (Paper 39), *Njoy, Inc.* v. *Fontem Holdings 1 B.V.*, IPR2014-01289 (P.T.A.B., petition filed Aug. 14, 2014), Mar. 1, 2018.
R.J. Reynolds Vapor Company, IPR2018-00627, Ex. 1011—Institution Decision dated Dec. 14, 2016 (Paper 11), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1012—Termination Order dated Jan. 5, 2017 (Paper 16), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1013—Institution Decision dated Dec. 29, 2016 (Paper 13), *Nu Mark LLC* v. *Fontem Holdings 1 B.V.*, IPR2016-01438 (P.T.A.B., petition filed Jul. 14, 2016), Mar. 1, 2018.
R.J. Reynolds Vapor Company, IPR2018-00627, Ex. 1014—Compilation of the 331 Patent File History, Mar. 1, 2018.
R.J. Reynolds Vapor Company, IPR2018-00627, Ex. 1015—U.S. Pat. No. 5,703,633 ("Gehrer"), Mar. 1, 2018.
R.J. Reynolds Vapor Company, IPR2018-00627, Ex. 1016—U.S. Pat. No. 5,745,985 ( "Ghosh"), Mar. 1, 2018.
R.J. Reynolds Vapor Company, IPR2018-00627, Ex. 1017—U.S. Pat. No. 4,208,005 ("Nate"), Mar. 1, 2018.
R.J. Reynolds Vapor Company, IPR2018-00627, Ex. 1018—U.S. Pat. No. 4,945,448 ("Bremenour"), Mar. 1, 2018.
R.J. Reynolds Vapor Company, IPR2018-00627, Ex. 1019—Excerpts from James W. Dally, *Packaging of Electronic Systems: A Mechanical Engineering Approach* (John Corrigan and John M. Morriss eds., 1990) ("Daily"), Mar. 1, 2018.
R.J. Reynolds Vapor Company, IPR2018-00627, Ex. 1020—U.S. Pat. No. 2,057,353 ("Whittemore"), Mar. 1, 2018.
R.J. Reynolds Vapor Company, IPR2018-00627, Ex. 1021—U.S. Pat. No. 3,200,819 ("Gilbert"), Mar. 1, 2018.
R.J. Reynolds Vapor Company, IPR2018-00627, Ex. 1022—U.S. Pat. No. 6,501,052 ("Cox 052"), Mar. 1, 2018.
R.J. Reynolds Vapor Company, IPR2018-00627, Ex. 1023—U.S. Pat. No. 6,234,167 ("Cox 167"), Mar. 1, 2018.
R.J. Reynolds Vapor Company, IPR2018-00627, Ex. 1024—U.S. Pat. No. 5,124,200 ("Mallonee"), Mar. 1, 2018.
R.J. Reynolds Vapor Company, IPR2018-00627, Ex. 1025—U.S. Pat. No. 4,797,692 ("Ims"), Mar. 1, 2018.
R.J. Reynolds Vapor Company, IPR2018-00627, Ex. 1026—U.S. Pat. No. 5,666,977 . ("Higgins"), Mar. 1, 2018.
R.J. Reynolds Vapor Company, IPR2018-00627, Ex. 1027—EP Pat. App. Pub. No. EP 0 358 114 A2 ("Brooks 114"), Mar. 1, 2018.
R.J. Reynolds Vapor Company, IPR2018-00627, Ex. 1028—U.S. Pat. No. 7,284,424 ("Kanke"), Mar. 1, 2018.
R.J. Reynolds Vapor Company, IPR2018-00627, Ex. 1029—U.S. Pat. No. 5,224,265 ("Dux"), Mar. 1, 2018.
R.J. Reynolds Vapor Company, IPR2018-00627, Ex. 1030—U.S. Pat. No. 6,620,659 ("Emmma"), Mar. 1, 2018.
R.J. Reynolds Vapor Company, IPR2018-00627, Ex. 1031—U.S. Pat. No. 4,676,237 ("Wood"), Mar. 1, 2018.
R.J. Reynolds Vapor Company, IPR2018-00627, Ex. 1032—Chinese Utility Model Pub. No. 1233436A ("Hongbin") (including certified translation), Mar. 1, 2018.
R.J. Reynolds Vapor Company, IPR2018-00627, Ex. 1033—Excerpts from *The Oxford American Dictionary and Thesaurus* (Ex. 2007), *Nu Mark LLC* v. *Fontem Holdings -1 B. V.*, IPR2016-01299 (P.T.A.B., petition filed Jun. 28, 2016), Mar. 1, 2018.
R.J. Reynolds Vapor Company, IPR2018-00627, Ex. 1035—Teleconference Transcript (Ex. 3001), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1036—Patent Owner's Preliminary Response to Petition for Inter Partes Review dated Oct. 7, 2016 (Paper 8), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1037—Excerpts from *Merriam-Webster's Collegiate Dictionary 11th ed.* (Ex. 2003), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1038—Excerpts from *Webster's Unabridged Dictionary 2nd ed.* (Ex. 2030), *Nu Mark LLC* v. *Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1039—Institution Decision dated Feb. 6, 2018 (Paper 8), *Samsung Elecs. Am.* v. *Uniloc*, IPR2017-01801 (P.T.A.B., petition filed Jul. 20, 2017), Mar. 1, 2018.
R.J. Reynolds Vapor Company, IPR2018-00627, Ex. 1040—Institution Decision dated Feb. 5, 2018 (Paper 9), *Cascades Canada ULC* v. *SCA Hygiene Prods AB*, IPR2017-01921 (P.T.A.B., petition filed Aug. 7, 2017), Mar. 1, 2018.
R.J. Reynolds Vapor Company, IPR2018-00627, Ex. 1041—Institution Decision dated Jan. 19, 2018 (Paper 9), *Donghee America, Inc.* v. *Plastic Omnium Advanced Innovation and Research*, IPR2017-01654 (P.T.A.B., petition filed Jun. 21, 2017), Mar. 1, 2018.
R.J. Reynolds Vapor Company, IPR2018-00627, Ex. 1042—Institution Decision dated May 18, 2017 (Paper 9), *Limelight Networks, Inc.* v. *Mass. Inst. of Tech.*, IPR2017-00249 (P.T.A.B., petition filed Nov. 11, 2016), Mar. 1, 2018.
R.J. Reynolds Vapor Company, IPR2018-00627, Ex. 1043—Institution Decision dated Jul. 15, 2015 (Paper 10), *Microsoft Corp.* v. *Parallel Networks Licensing, LLC*, IPR2015-00483 (P.T.A.B., petition filed Dec. 23, 2014), Mar. 1, 2018.
R.J. Reynolds Vapor Company, IPR2018-00627, Ex. 1044—Institution Decision dated Mar. 13, 2013 (Paper 19), *Micron Tech., Inc.* v. *Bd. of Trs. of the Univ. of Ill.*, IPR2013-00005 (P.T.A.B., petition filed Oct. 2, 2012), Mar. 1, 2018.
R.J. Reynolds Vapor Company, IPR2018-00627, Ex. 1045—Institution Decision dated Jan. 24, 2013 (Paper 18), *Macauto U.S.A.* v. *BOS GMBH & KG*, IPR2012-00004 (P.T.A.B., petition filed Sep. 16, 2012), Mar. 1, 2018.
R.J. Reynolds Vapor Company, IPR2018-00627, Ex. 1046—Institution Decision dated Dec. 30, 2016 (Paper 11), *R.J. Reynolds Vapor Co.* v. *Fontem Holdings 1 B.V.*, IPR2016-01272 (P.T.A.B., petition filed Jul. 2, 2016), Mar. 1, 2018.
R.J. Reynolds Vapor Company, IPR2018-00627, Ex. 1047—Final Written Decision dated Jan. 25, 2016 (Paper 39), *Google, Inc.* v. *Visual Real Estate, Inc.*, IPR2014-01339 (P.T.A.B., petition filed Aug. 20, 2014), Mar. 1, 2018.

(56) References Cited

OTHER PUBLICATIONS

R.J. Reynolds Vapor Company, IPR2018-00627, Ex. 1048—Final Written Decision dated Feb. 17, 2016 (Paper 40), *Cisco Sys., Inc., et al.* v. *Capella Photonics, Inc.*, IPR2014-01276 (P.T.A.B., petition filed Aug. 12, 2014), Mar. 1, 2018.
R.J. Reynolds Vapor Company, IPR2018-00627, Ex. 1049—Final Written Decision dated Mar. 28, 2016 (Paper 20), *RF Controls, LLC* v. *A-1 Packaging Sols., Inc.*, IPR2014-01536 (P.T.A.B., petition filed Sep. 23, 2014), Mar. 1, 2018.
Case 1:16-cv-01255-CCE-JEP, Dkt. No. 148., *Fontem Ventures B.V. and Fontem Holdings 1 B.V.* v. *R.J. Reynolds Vapor Company*, Claim Construction Order, Mar. 12, 2018, 8 pages.
Case 2:14-cv-01645-GW-MRW, Dkt. No. 65, *Fontem Ventures B.V. et al.* v. *Njoy, Inc. et al.* Court's Rulings on Claims Construction, Jan. 29, 2015, 28 pages.
Case No. CV14/1645-GW(MRWx), Dkt. No. 133, *Fontem Ventures B.V. et al.* v. *Njoy, Inc. et al.* Order regarding Markman Hearing/Claim Construction, May 7, 2015, 16 pages.
R.J. Reynolds Vapor Company, Preliminary Invalidity Contentions for 17-cv-0175, Jul. 31, 2017.
R.J. Reynolds Vapor Company, Preliminary Invalidity Contentions, Exhibit F (U.S. Pat. No. 8,393,331), 17-cv-0175, Jul. 31, 2017.
USPTO, Notice of Allowance for U.S. Appl. No. 15/167,825, dated Jun. 2, 2017.
USPTO, Office Action for U.S. Appl. No. 14/525,066, dated Sep. 28, 2017.
USPTO, Office Action for U.S. Appl. No. 15/167,825, dated Sep. 9, 2016.
R.J. Reynolds Vapor Company, Final Invalidity Contentions served in *Fontem Holdings B.V.* v. *R.J. Reynolds Vapor Company*, U.S. District Court for the Middle District of North Carolina, Case No. 16-cv-1255 and consolidated cases (relating to U.S. Pat. No. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Elections served in *Fontem Holdings B.V.* v. *R.J. Reynolds Vapor Company*, U.S. District Court for the Middle District of North Carolina, Case No. 16-cv-1255 and consolidated cases (relating to U.S. Pat. No. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Contentions, 16-cv-1255 and consolidated cases, Amended Exhibit F (U.S. Pat. No. 8,393,331), May 7, 2018.
R.J. Reynolds Vapor Company, Final Invalidity Contentions served in *Fontem Holdings B.V.* v. *R.J. Reynolds Vapor Company*, U.S. District Court for the Middle District of North Carolina, Case No. 16-cv-1255 and consolidated cases (relating to U.S. Pat. No. 8,365,742, 8,490,628, 8,893,726, 8,899,239, 8,326,548, 8,326,549, and 9,370,205), May 7, 2018.
R.J. Reynolds Vapor Company, Final Invalidity Elections served in *Fontem Holdings B.V.* v. *R.J. Reynolds Vapor Company*, U.S. District Court for the Middle District of North Carolina, Case No. 16-cv-1255 and consolidated cases (relating to U.S. Pat. No. 8,365,742, 8,490,628, 8,893,726, 8,899,239, 8,326,548, 8,326,549, and 9,370,205), May 7, 2018.
R.J. Reynolds Vapor Company, Final Invalidity Contentions, 16-cv-1255 and consolidated cases, Amended Exhibit B (U.S. Pat. No. 8,490,628), May 7, 2018.
R.J. Reynolds Vapor Company, Final Invalidity Contentions, 16-cv-1255 and consolidated cases, Amended Exhibit C (U.S. Pat. No. 8,893,726), May 7, 2018.
R.J. Reynolds Vapor Company, Final Invalidity Contentions, 16-cv-1255 and consolidated cases, Amended Exhibit F (U.S. Pat. No. 8,326,549), May 7, 2018.
USPTO, U.S. Appl. No. 15/900,430, Non-Final Office Action, dated May 9, 2018.
USPTO, U.S. Appl. No. 14/525,066, Non-Final Office Action, dated May 15, 2018.

ELECTRONIC CIGARETTE

CROSS REFERENCE TO RELATED APPLICATIONS

This application is a Continuation of U.S. patent application Ser. No. 14/525,066, filed Oct. 27, 2014, and now pending, which is a Continuation of U.S. patent application Ser. No. 13/777,927, filed Feb. 26, 2013, now U.S. Pat. No. 8,893,726, which is a Divisional of U.S. patent application Ser. No. 13/560,789, filed Jul. 27, 2012 and now U.S. Pat. No. 8,490,628, which is a Continuation of U.S. patent application Ser. No. 12/944,123, filed Nov. 11, 2010 and now U.S. Pat. No. 8,393,331, which is a Continuation of U.S. patent application Ser. No. 10/587,707, filed Mar. 9, 2007, now U.S. Pat. No. 7,832,410 which is the U.S. National Phase Application of International PCT Application No. PCT/CN05/00337, filed Mar. 18, 2005, which claims the benefit of Chinese Patent Application No. 200420031182.0, filed Apr. 14, 2004, all of which are incorporated herein by reference in their entirety.

TECHNICAL FIELD

The present invention relates to an electronic cigarette, in particular to an electronic atomization cigarette that contains only nicotine without tar.

BACKGROUND ART

Although it is commonly known that "smoking is harmful to your health", the number of smokers worldwide is up to 1 billion, and the number is increasing every year. According to the statistical data from the World Health Organization, about 4.9 million people die of smoking diseases each year. Although smoking may cause serious respiratory diseases and cancer, it remains extremely difficult for smokers to quit smoking completely.

The active ingredient in a cigarette is nicotine. During smoking, nicotine, along with tar aerosol droplets, enter the smoker's alveolus and are rapidly absorbed. The nicotine then affects the receptors of the smoker's central nervous system.

Nicotine is a kind of alkaloid with low molecular weight. A small dose of nicotine is essentially harmless to human body and its half-life in blood is quite short. The major harmful substance in tobacco is tar. Tar in tobacco is composed of thousands of ingredients. Several of these are cancerogenic.

Some cigarette substitutes that contain only nicotine without tar have been proposed. Many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration cannot be reached in the blood of a smoker due to slow absorption of nicotine In addition, these cigarette substitutes cannot satisfy habitual smoking actions of a smoker, for example, inhaling action, and thus are not likely to be widely accepted as effective substitutes for smoking.

THE SUMMARY OF THE INVENTION

An electronic atomization cigarette that functions as substitutes for quitting smoking and cigarette substitutes includes a shell; a mouthpiece; an air inlet provided in the external wall of the shell; an electronic circuit board, a sensor, an atomizer, and a liquid-supply within the shell. A stream passage is provided on one side of the sensor. An atomization cavity is arranged in the atomizer. The liquid-supply is in contact with the atomizer.

DETAILED DESCRIPTION

Embodiment 1

Figure 1:
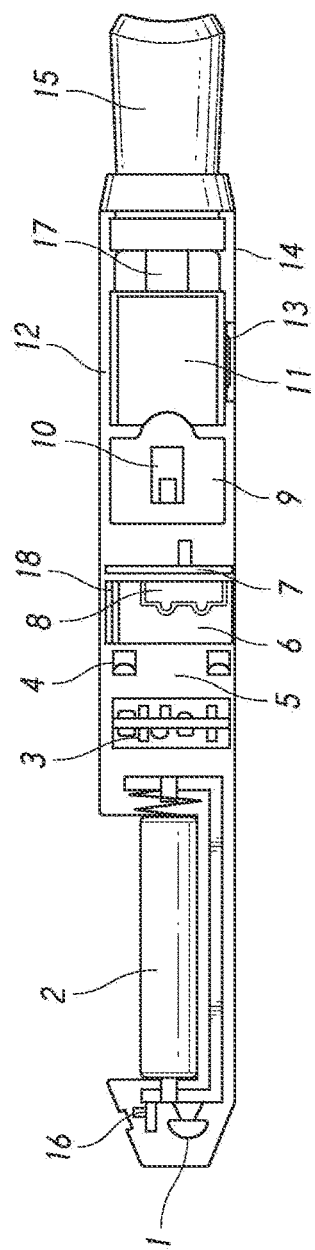
FIG. 1 is a schematic diagram of an overall structure.

As shown in FIG. 1, an air inlet 4 is provided on the external wall of the shell 14. A LED 1, a cell 2, an electronic circuit board 3, a normal pressure cavity 5, a sensor 6, a vapor-liquid separator 7, an atomizer 9, a liquid-supplying bottle 11 and a mouthpiece 15 are sequentially provided within the shell 14. The electronic circuit board 3 comprises an electronic switching circuit and a high frequency generator.

Figure 4:
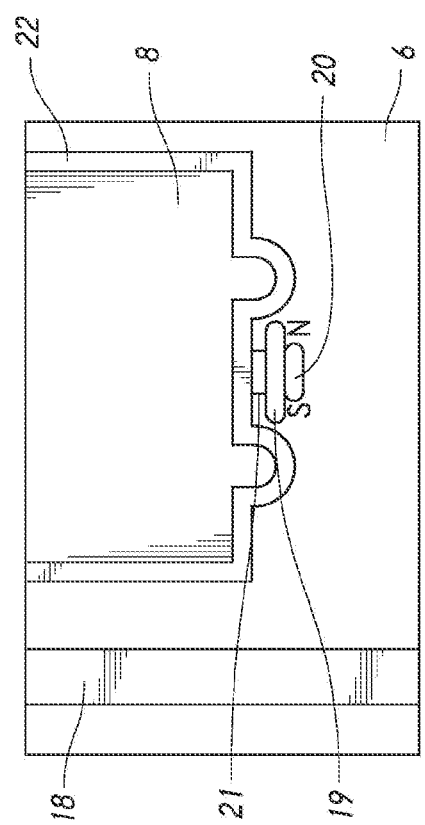
FIG. 4 is a structural diagram of a sensor.

As shown in FIG. 4, a negative pressure cavity 8 is provided in the sensor 6 and is separated from the sensor 6 by a film 22 A first magnetic steel 20, a second magnetic steel 21 and a Reed switch 19 arranged between them is also provided within the sensor 6. The second magnetic steel 21 is attached to the film 22. The atomizer 9 is in contact with the liquid-supplying bottle 11 via the bulge 36, and the atomization cavity 10 is provided in the atomizer 9.

Figure 6:
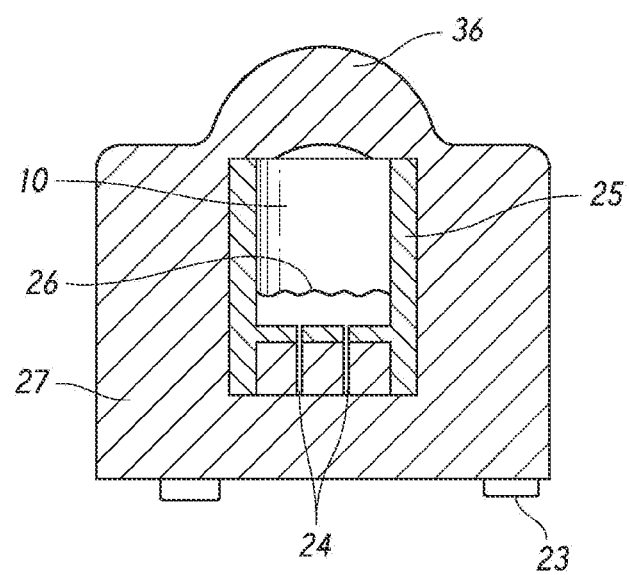
FIG. 6 is a structural diagram of an atomizer.
Figure 7:
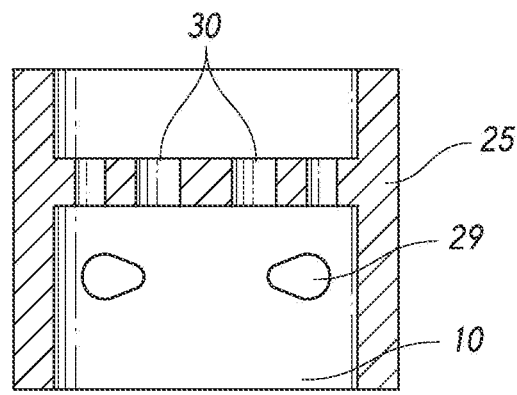
FIG. 7 is a structural diagram of the ceramic member in an atomizer.

As shown in FIGS. 6 and 7, the overflow hole 29 is provided on the wall 25 of the atomization cavity 10. A heating element 26, which can be made of platinum wire, nickel chromium alloy or iron chromium aluminum alloy wire with rare earth element, is provided within the cavity, and can also be made into a sheet form with conductive ceramics or PTC ceramics. An ejection hole is provided on the side opposite to the heating element 26. The ejection hole can be determined to select either the long stream ejection hole 24 or the short stream ejection hole 30, depending on the material used for the atomization cavity wall 25. The long stream ejection hole 24 can employ slot structure of 0.1 mm-1.3 mm or circular hole structure with a single and multiple holes. The short stream ejection hole 30 has the diameter of about 0.3 mm-1.3 mm.

Figure 2:
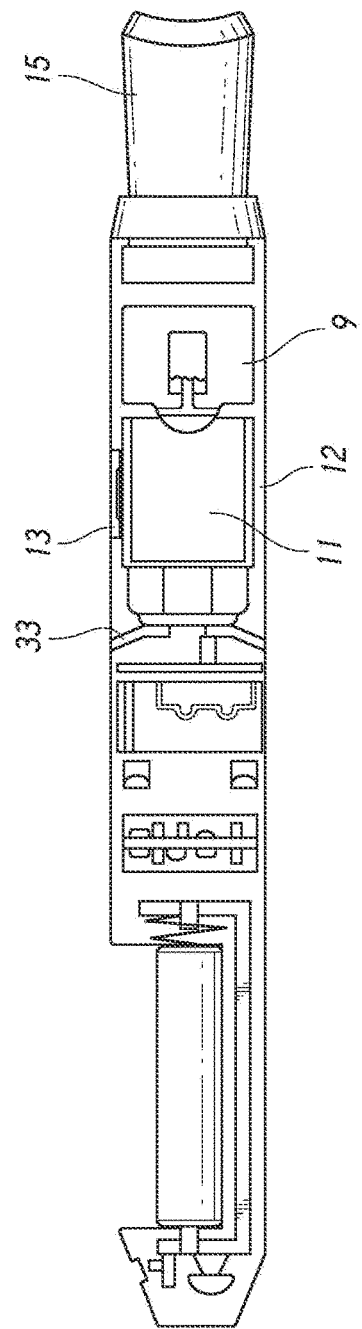
FIG. 2 is a schematic diagram of another overall structure.
Figure 3:
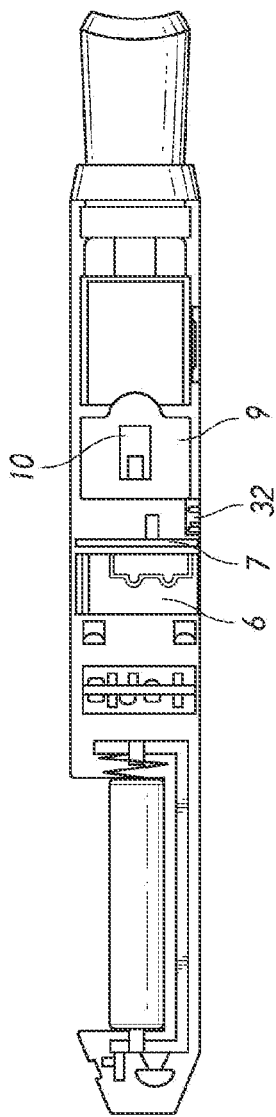
FIG. 3 is a schematic diagram of an overall structure with a display screen.
Figure 9:
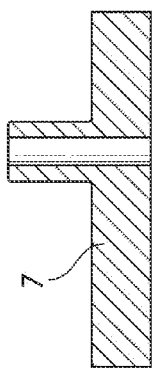
FIG. 9 is a structural diagram of a vapor-liquid separator.

The atomization cavity wall 25 is surrounded with the porous body 27, which can be made of foam nickel, stainless steel fiber felt, high molecule polymer foam and foam ceramic. A first piezoelectric element 23 is also provided on the atomizer 9. The atomization cavity wall 25 can be made of aluminum oxide or ceramic. As shown in FIG. 9, a through hole is provided on the vapor-liquid separator 7, and can be made of plastic or silicon rubber. As shown in FIG. 2, a retaining ring 13 for locking the liquid-supplying bottle 11 is provided between one side of the liquid-supplying bottle 11 and the shell 14. An aerosol passage 12 is provided on the other side of the liquid-supplying bottle.

Figure 11:
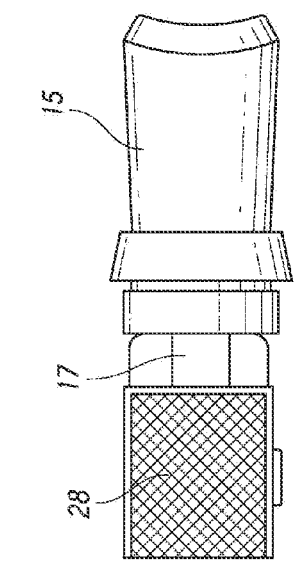
FIG. 11 is a structural diagram of the connection of a liquid-supplying bottle and a mouthpiece.

As shown in FIG. 11, the solution storage porous body 28 is provided in the liquid-supplying bottle, and can be filled with polypropylene fiber, terylene fiber or nylon fiber, or be filled with plastic shaped by foaming, such as polyamine resin foam column or polypropylene foam column. Alternatively, it may be made of a column formed by molding polyvinyl chloride, polypropylene, polycarbonate into a stack of laminated layers. The air inlet 4, normal pressure cavity 5, vapor-liquid separator 7, atomizer 9, aerosol passage 12, gas vent 17, mouthpiece 15 are sequentially interconnected.

Figure 12:
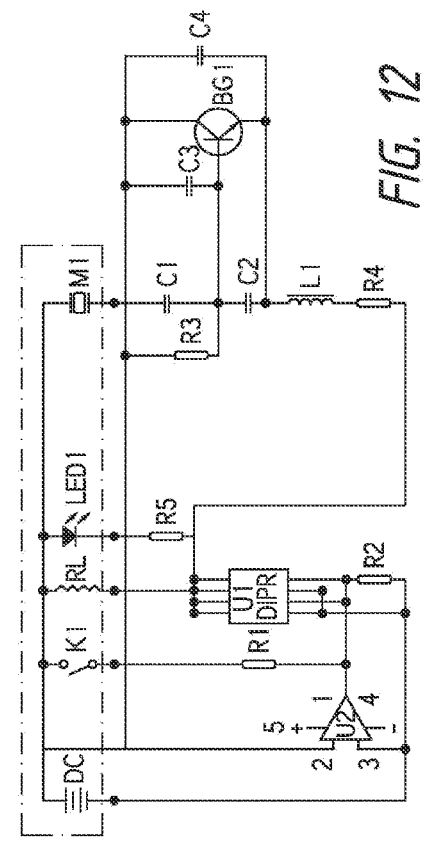
FIG. 12 is a functional diagram of a circuit.

As shown in the functional diagram of the circuit in FIG. 12, K1 refers to the Reed switch 19, RL refers to the heating element 26, LED1 refers to the Light Emitting Diode 1, U2 refers to the low voltage detecting element used for the over-discharging protection of the lithium cell, M1 refers to the first piezoelectric element 23, and C1, C2, R3, L1, C3, BG, M1 collectively constitute a Colpitts oscillator. The operating principle of the circuit is as follows: when K1 is closed, U1, i.e., the field effect power transistor, is turned on, RL starts, and the Colpitts oscillator starts oscillating, M1 will provide the high frequency mechanical oscillatory wave to the atomizer 9.

When a smoker smokes, the mouthpiece 15 is under negative pressure. The air pressure difference or high speed stream between the normal pressure cavity 5 and the negative pressure cavity 8 causes the sensor 6 to output an actuating signal, the electronic circuit board 3 connected therewith goes into operation. Now the ripple film 22 in the sensor 6 is deformed to take the second magnetic steel 21 away from the Reed switch 19. The Reed switch 19 is then closed (i.e., K1 is closed) under the effect of the excessive magnetic line of force from the first magnetic steel 20, starting the field effect power transistor electronic switch (i.e., U1 is opened). The high frequency oscillator may uses the Colpitts oscillator with the frequency of 550 KHz-8 MHz. The automatic fine-adjusting element in the circuit resonates with the first piezoelectric element 23. The LED 1 can be lit under the supply of the rechargeable battery 2.

Air enters the normal pressure cavity 5 through the air inlet 4, passes through the air passage 18 of the sensor and then the through hole in the vapor-liquid separator 7, and flows into the atomization cavity 10 in the atomizer 9. The high speed stream passing through the ejection hole drives the nicotine solution in the porous body 27 to eject into the atomization cavity 10 in the form of droplets, where the nicotine solution is subjected to the ultrasonic atomization by the first piezoelectric element 23 and is further atomized by the heating element 26.

After the atomization the droplets with large diameters stick to the wall under the action of eddy flow and are reabsorbed by the porous body 27 via the overflow hole 29. Droplets with small diameters float in stream and form aerosols, which are sucked out via the aerosol passage 12, gas vent 17 and mouthpiece 15. The solution storage porous body 28 in the liquid-supplying bottle 11 is in contact with the bulge 36 on the atomizer 9, thereby achieving the capillary infiltration liquid-supplying.

The mouthpiece 15 is threaded. When the nicotine solution in the liquid-supplying bottle 11 is used up, users can screw the mouthpiece 15 out to take the liquid-supplying bottle 11 out, refill the liquid-supplying bottle 11 with the nicotine solution, put the liquid-supplying bottle 11 into the shell 14 again, and then screw the mouthpiece 15.

The Reed switch 19, the first magnetic steel 20, the second magnetic steel 21, the ripple film 22 can be replaced by a semiconductor strain gauge with sealed film, which is mounted in the place of the sensor ripple film.

Figure 8:
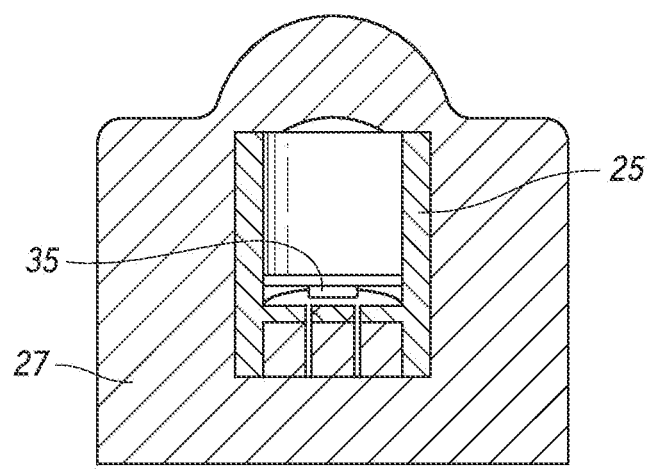
FIG. 8 is a structural diagram of another atomizer.

To simplify the design, the first piezoelectric element 23 on the atomizer 9 can be omitted, and the atomization of the nicotine solution will be made only by the heating element 26. The size of such an atomizer can be made smaller, and the structure of the connection of the whole electronic atomization cigarette is the same as the embodiment 1. In addition, as shown FIG. 8, the first piezoelectric element 23 and the heating element 26 in the atomizer 9 can be omitted, an additional second piezoelectric element 35 in the form of platen with a single layer or multiple laminated layers can be arranged in the atomization cavity, and the stream passing through the ejection hole vibrates the focus at the center of the second piezoelectric element 35 to achieve the effect of strong ultrasonic atomization.

Figure 10:
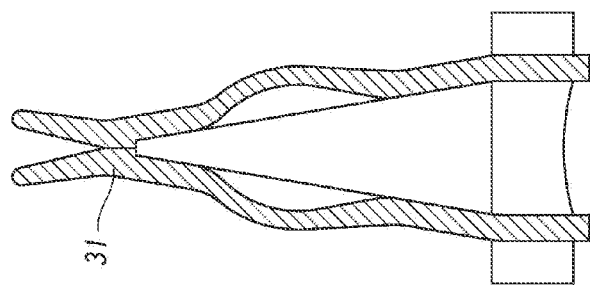
FIG. 10 is a structural diagram of another vapor-liquid separator.

As shown in FIG. 10, a silicon gel check valve 31 may cover the outside of the through hole on the vapor-liquid separator 7. During smoking, a stream reaches the through hole, as the air pressure in the through hole increases, the silicon gel check valve 31 is opened and the stream passes; otherwise, the silicon gel check valve 31 is closed.

Figure 5:
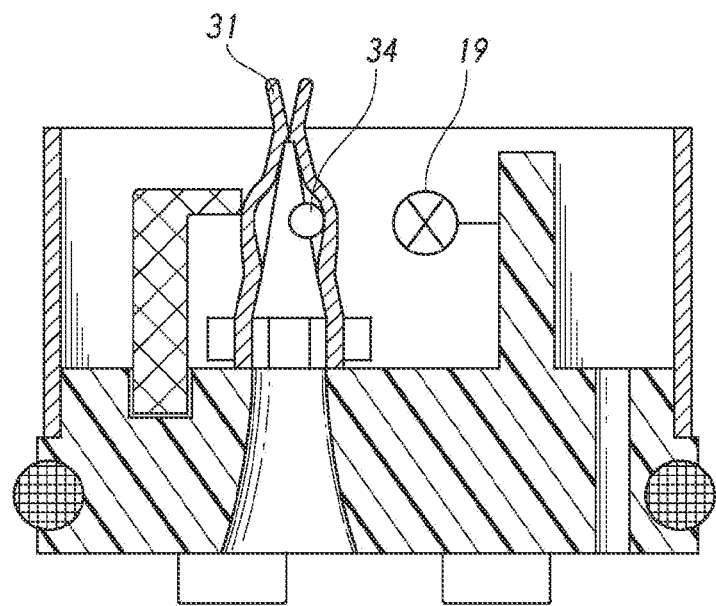
FIG. 5 is a structural diagram of a sensor with a silicon gel check valve.

As shown in FIG. 5, the sensor 6 may also be designed into a structure with the silicon gel check valve 31. During smoking, the stream comes into the silicon gel check valve 31, the air pressure increases and the air expands, the third magnetic steel 34 in the valve approaches the Reed switch 19 gradually until the Reed switch is closed and the circuit is turned on, and the air outlet of the silicon gel check valve 31 is opened with the increment of the air pressure difference. The Reed switch 19 can also be made of Hall device or magneto diode or magneto triode instead.

Embodiment 2

As shown in FIG. 2, to improve the liquid-supplying state, the liquid-supplying bottle 11 is arranged between the vapor-liquid separator 7 and the atomizer 9. A spring piece 33 for pressing the liquid-supplying bottle 11 on the atomizer 9 is provided on one end of the liquid-supplying bottle 11. Other components and their functions are the same as those in the embodiment 1.

On the inner wall of the shell 14 of the electronic atomization cigarette described in the embodiment 1 and 2, a digital display screen 32 for showing the smoking times per day and the cell capacity can be also provided. The sensor 6 uses a linear signal output, which is proportional to the suction force (i.e., the stronger one sucks, the longer the time of operation is), the atomizer 9 operates in the linear mode, thereby simulating a cigarette that looks like a normal cigarette.

Within the shell 14, the microswitch 16 is connected to the sensor 6 in parallel and used for manually cleaning. When users do not smoke, they press the microswitch 16 to start the sensor 6 connected therewith in parallel, or clean the residue or other impurity substance within the shell 14.

The nicotine solution for atomization contains 0.4-3.5% nicotine, 0.05-2% cigarette essence, 0.1-3.1% organic acid, 0.1-0.5% anti-oxidation agent, and the rest is 1,2-propylene glycol.

The invention claimed is:

1. A vaporizing device, comprising:
a housing having a battery and an LED electrically connected to an electronic circuit board;
an atomizer having a heating wire positioned in a cavity with the heating wire extending and oriented in a direction perpendicular to a longitudinal axis of the housing;
a removable liquid supply assembly having a liquid container, a first end and a second end;
an air flow passage from an inlet to an outlet in a mouthpiece at the second end of the removable liquid supply assembly, the air flow passage including an aerosol passage from the atomizer to the outlet; and
a retaining element on a side of the liquid container, the first end of the removable liquid supply assembly configured to be inserted into the housing;
the liquid container adapted to hold liquid; and
a porous component for moving liquid from the liquid container to the heating wire.

2. The vaporizing device of claim 1 wherein the retaining element retains the liquid container in the housing.

3. The vaporizing device of claim 2 further including a manually operated switch electrically connected to the electronic circuit board.

4. The vaporizing device of claim 1 wherein the air flow passage extends through the atomizer to the mouthpiece.

5. The vaporizing device of claim 2 with the porous component comprising a fiber material.

6. The vaporizing device of claim 5 with the heating wire in the air flow passage.

7. The vaporizing device of claim 2 with the liquid container comprising a re-fillable bottle.

8. The vaporizing device of claim 2 wherein the liquid is vaporized via heating the heating wire.

9. The vaporizing device of claim 2 further comprising propylene glycol in the liquid container.

10. The vaporizing device of claim 2 further including a gas vent leading into the mouthpiece co-axial with the longitudinal axis of the housing.

11. A vaporizing device, comprising:
a housing having a battery connected to an electronic circuit board;
a heating wire positioned in a cavity, the heating wire extending and oriented in a direction perpendicular to a longitudinal axis of the housing;
an air flow passage from an inlet to an outlet;
a removable liquid supply assembly having a mouthpiece and a liquid container, a first end and a second end, an aerosol passage leading to the outlet through the mouthpiece at the second end of the removable liquid supply assembly;
a retaining element for retaining the removable liquid supply assembly in the housing;
the first end of the removable liquid supply assembly configured to be inserted into the housing;
the liquid container adapted to hold liquid; and
a porous component for moving liquid from the liquid container to the heating wire.

12. The vaporizing device of claim 11 with the aerosol passage on a first side of the liquid container and the retaining element on a second side of the liquid container opposite from the first side.

13. The vaporizing device of claim 11 with the porous component comprising a fiber material.

14. The vaporizing device of claim 11 with the heating wire in the air flow passage and the air flow passage extending through an atomizer to the mouthpiece.

15. The vaporizing device of claim 14 further including a gas vent leading into the mouthpiece co-axial with the longitudinal axis of the housing.

16. The vaporizing device of claim 11 further including a manually operated switch electrically connected to the electronic circuit board.

17. The vaporizing device of claim 11 further including a sensor electrically connected to the electronic circuit board.

18. A vaporizing device, comprising:
a housing having a battery and an LED electrically connected to an electronic circuit board;
a manually operated switch electrically connected to the electronic circuit board;
an atomizer having a heating wire positioned in a cavity, with the heating wire extending and oriented in a direction perpendicular to a longitudinal axis of the housing;
an air flow passage from an inlet to an outlet, with the heating wire in the air flow passage and the air flow passage extending through the atomizer;
a removable liquid supply assembly having a liquid container, a first end and a second end, an aerosol passage on a first side of the liquid container leading to the outlet through a mouthpiece at the second end of the removable liquid supply assembly;
a retaining element on a second side of the liquid container opposite from the first side, for retaining the removable liquid supply assembly to the housing, the first end of the removable liquid supply assembly configured to be inserted into the housing;
the liquid container adapted to hold liquid; and
a porous component for moving liquid from the liquid container to the heating wire, wherein the liquid is vaporized via heating the heating wire.

19. The vaporizing device of claim 18 with the liquid container comprising a re-fillable bottle.

* * * * *